(12) United States Patent
Bauer et al.

(10) Patent No.: US 8,026,091 B2
(45) Date of Patent: Sep. 27, 2011

(54) DNA POLYMERASES AND RELATED METHODS

(75) Inventors: Keith A. Bauer, San Rafael, CA (US); David Harrow Gelfand, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 506 days.

(21) Appl. No.: 12/170,110

(22) Filed: Jul. 9, 2008

(65) Prior Publication Data
US 2009/0137000 A1    May 28, 2009

Related U.S. Application Data

(60) Provisional application No. 60/949,732, filed on Jul. 13, 2007.

(51) Int. Cl.
*C12N 9/12* (2006.01)
*C12P 19/34* (2006.01)

(52) U.S. Cl. .................. 435/194; 435/183; 435/91.1

(58) Field of Classification Search .................. None
See application file for complete search history.

(56) References Cited

FOREIGN PATENT DOCUMENTS

| EP | 0 745 675 | 12/1996 |
|---|---|---|
| EP | 1 152 062 | 11/2001 |
| WO | WO 01/51621 | 7/2001 |
| WO | WO 2005/045015 | 5/2005 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
U.S. Appl. No. 11/873,896, filed Oct. 18, 2007.

* cited by examiner

*Primary Examiner* — Richard Hutson
(74) *Attorney, Agent, or Firm* — Kilpatrick Townsend & Stockton, LLP

(57) ABSTRACT

Disclosed are mutant DNA polymerases having improved extension rates relative to a corresponding, unmodified polymerase. The mutant polymerases are useful in a variety of disclosed primer extension methods. Also disclosed are related compositions, including recombinant nucleic acids, vectors, and host cells, which are useful, e.g., for production of the mutant DNA polymerases.

16 Claims, 8 Drawing Sheets

|        |                              |
|--------|------------------------------|
| Tth    | FRLAGHPFNLNSRDQLERVLFDELRL   |
| Tca    | FRLAGHPFNLNSRDQLERVLFDELRL   |
| Z05    | FRLAGHPFNLNSRDQLERVLFDELRL   |
| Taq    | FRLAGHPFNLNSRDQLERVLFDELGL   |
| Tfl    | FRLAGHPFNLNSRDQLERVLFDELGL   |
| Tfi    | HRLAGHPFNLNSRDQLERVLFDELGL   |
| Sps17  | HRLAGHPFNLNSRDQLERVLFDELGL   |
| Dra    | HEYAGEEFHIRSPKQLETVLYDKLEL   |
| HspB7  | YTLAGEAFNIGSPKQLGAILFEKLGL   |
| Bst    | YELAGQEFNINSPKQLGTVLFDKLQL   |
| Bca    | YELAGQEFNINSPKQLGVILFEKLQL   |
| Eco    | HEIAGEEFNLSSTKQLQTILFEKQGI   |
| Tma    | YRIAGEPFNINSPKQVSRILFEKLGI   |
| Tne    | YQIAGEPFNINSPKQVSNILFEKLGI   |
| Taf    | FEIAGETFNLNSSTQVAYILFEKINI   |
| HspA   | YAQAGEVFNLNSPKQLGSLLFEKLKL   |
| CS5    | YRIAGEPFNINSPKQVSRILFEKLGI   |
| CS6    | YRIAGEPFNINSPKQVSRILFEKLGI   |
| T7     | VEHVV..FNPSSRDHIQKKLQEAGWV   |
| Cons   | ---AG--FN--S--Q-----LF--L--  |

Figure 1

```
  1  MKAMLPLFEP KGRVLLVDGH HLAYRTFFAL KGLTTSRGEP VQAVYGFAKS
 51  LLKALKEDGY KAVFVVFDAK APSFRHEAYE AYKAGRAPTP EDFPRQLALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
251  RSDLPLEVDF ARRREPDREG LRAFLERLEF GSLLHEFGLL EESEPVGYRI
301  VKDLVEFEKL IEKLRESPSF AIDLETSSLD PFDCDIVGIS VSFKPKEAYY
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
851  ELVFEVPNEE KDALVELVKD RMTNVVKLSV PLEVDVTIGK TWS
```

Figure 2A

```
   1  ATGAAAGCTA TGTTACCATT ATTCGAACCC AAAGGCCGGG TCCTCCTGGT
  51  GGACGGCCAC CACCTGGCCT ACCGCACCTT CTTCGCCCTG AAGGGCCTCA
 101  CCACGAGCCG GGGCGAACCG GTGCAGGCGG TTTACGGCTT CGCCAAGAGC
 151  CTCCTCAAGG CCCTGAAGGA GGACGGGTAC AAGGCCGTCT TCGTGGTCTT
 201  TGACGCCAAG GCCCCTTCCT TCCGCCACGA GGCCTACGAG GCCTACAAGG
 251  CAGGCCGCGC CCCGACCCCC GAGGACTTCC CCGGCAGCT CGCCCTCATC
 301  AAGGAGCTGG TGGACCTCCT GGGGTTTACT CGCCTCGAGG TTCCGGGCTT
 351  TGAGGCGGAC GACGTCCTCG CCACCCTGGC CAAGAAGGCG AAAGGGAGG
 401  GGTACGAGGT GCGCATCCTC ACCGCCGACC GGGACCTTTA CCAGCTCGTC
 451  TCCGACCGCG TCGCCGTCCT CCACCCCGAG GGCCACCTCA TCACCCCGGA
 501  GTGGCTTTGG GAGAAGTACG GCCTTAAGCC GGAGCAGTGG GTGGACTTCC
 551  GCGCCCTCGT GGGGGACCCC TCCGACAACC TCCCCGGGGT CAAGGGCATC
 601  GGGGAGAAGA CCGCCCTCAA GCTCCTCAAG GAGTGGGGAA GCCTGGAAAA
 651  TATCCTCAAG AACCTGGACC GGGTGAAGCC GGAAAGCGTC CGGGAAAGGA
 701  TCAAGGCCCA CCTGGAAGAC CTTAAGCTCT CCTTGGAGCT TTCCCGGGTG
 751  CGCTCGGACC TCCCCCTGGA GGTGGACTTC GCCCGGAGGC GGGAGCCTGA
 801  CCGGGAAGGG CTTCGGGCCT TTTTGGAGCG CTTGGAGTTC GGCAGCCTCC
 851  TCCACGAGTT CGGCCTTCTA GAGGAGTCCG AACCCGTTGG GTACCGTATA
 901  GTTAAAGACC TGGTTGAATT TGAAAAACTC ATAGAGAAAC TGAGAGAATC
 951  TCCTTCGTTC GCTATCGATT TGGAAACTAG TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AAGAGGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
```

Figure 2B-1

```
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AAGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

Figure 2B-2

```
  1  MKAMLPLFEP KGRVLLVDGH HLAYRTFFAL KGLTTSRGEP VQAVYGFAKS
 51  LLKALKEDGY KAVFVVFDAK APSFRHEAYE AYKAGRAPTP EDFPRQLALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
251  RSDLPLEVDF ARRREPDREG LRAFLERLEF GSLLHEFGLL EESEPVGYRI
301  VKDLVEFEKL IEKLRESPSF AIALATSSLD PFDCDIVGIS VSFKPKEAYY
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
852  ELVFEVPNEE KDALVELVKD RMTNVVKLSV PLEVDVTIGK TWS
```

Figure 3A

```
   1   ATGAAAGCTA TGTTACCATT ATTCGAACCC AAAGGCCGGG TCCTCCTGGT
  51   GGACGGCCAC CACCTGGCCT ACCGCACCTT CTTCGCCCTG AAGGGCCTCA
 101   CCACGAGCCG GGGCGAACCG GTGCAGGCGG TTTACGGCTT CGCCAAGAGC
 151   CTCCTCAAGG CCCTGAAGGA GGACGGGTAC AAGGCCGTCT TCGTGGTCTT
 201   TGACGCCAAG GCCCCTTCCT TCCGCCACGA GGCCTACGAG GCCTACAAGG
 251   CAGGCCGCGC CCCGACCCCC GAGGACTTCC CCGGCAGCT CGCCCTCATC
 301   AAGGAGCTGG TGGACCTCCT GGGGTTTACT CGCCTCGAGG TTCCGGGCTT
 351   TGAGGCGGAC GACGTCCTCG CCACCCTGGC CAAGAAGGCG AAAGGGAGG
 401   GGTACGAGGT GCGCATCCTC ACCGCCGACC GGGACCTTTA CCAGCTCGTC
 451   TCCGACCGCG TCGCCGTCCT CCACCCCGAG GGCCACCTCA TCACCCCGGA
 501   GTGGCTTTGG GAGAAGTACG GCCTTAAGCC GGAGCAGTGG GTGGACTTCC
 551   GCGCCCTCGT GGGGGACCCC TCCGACAACC TCCCCGGGGT CAAGGGCATC
 601   GGGGAGAAGA CCGCCCTCAA GCTCCTCAAG GAGTGGGGAA GCCTGGAAAA
 651   TATCCTCAAG AACCTGGACC GGGTGAAGCC GGAAAGCGTC CGGGAAAGGA
 701   TCAAGGCCCA CCTGGAAGAC CTTAAGCTCT CCTTGGAGCT TTCCCGGGTG
 751   CGCTCGGACC TCCCCCTGGA GGTGGACTTC GCCCGGAGGC GGGAGCCTGA
 801   CCGGGAAGGG CTTCGGGCCT TTTTGGAGCG CTTGGAGTTC GGCAGCCTCC
 851   TCCACGAGTT CGGCCTTCTA GAGGAGTCCG AACCCGTTGG GTACCGTATA
 901   GTTAAAGACC TGGTTGAATT TGAAAAACTC ATAGAGAAAC TGAGAGAATC
 951   TCCTTCGTTC GCGATCGCTC TTGCGACTAG TTCCCTCGAT CCTTTCGACT
1001   GCGACATTGT CGGTATCTCT GTGTCTTTCA ACCAAAGGA AGCGTACTAC
1051   ATACCACTCC ATCATAGAAA CGCCCAGAAC CTGGACGAAA AGAGGTTCT
1101   GAAAAGCTC AAAGAAATTC TGGAGGACCC CGGAGCAAAG ATCGTTGGTC
1151   AGAATTTGAA ATTCGATTAC AAGGTGTTGA TGGTGAAGGG TGTTGAACCT
1201   GTTCCTCCTT ACTTCGACAC GATGATAGCG GCTTACCTTC TTGAGCCGAA
1251   CGAAAAGAAG TTCAATCTGG ACGATCTCGC ATTGAAATTT CTTGGATACA
1301   AAATGACATC TTACCAAGAG CTCATGTCCT TCTCTTTTCC GCTGTTTGGT
```

Figure 3B-1

```
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AAGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

Figure 3B-2

DNA POLYMERASES AND RELATED METHODS

CROSS-REFERENCE TO RELATED PATENT APPLICATIONS

The present invention claims benefit of priority to U.S. Provisional Patent Application No. 60/949,732, filed Jul. 13, 2007, which is incorporated by reference in its entirety for all purposes.

FIELD OF THE INVENTION

The present invention lies in the field of DNA polymerases and their use in various applications, including nucleic acid primer extension and amplification.

BACKGROUND OF THE INVENTION

DNA polymerases are responsible for the replication and maintenance of the genome, a role that is central to accurately transmitting genetic information from generation to generation. DNA polymerases function in cells as the enzymes responsible for the synthesis of DNA. They polymerize deoxyribonucleoside triphosphates in the presence of a metal activator, such as $Mg^{2+}$, in an order dictated by the DNA template or polynucleotide template that is copied. In vivo, DNA polymerases participate in a spectrum of DNA synthetic processes including DNA replication, DNA repair, recombination, and gene amplification. During each DNA synthetic process, the DNA template is copied once or at most a few times to produce identical replicas. In contrast, in vitro, DNA replication can be repeated many times such as, for example, during polymerase chain reaction (see, e.g., U.S. Pat. No. 4,683,202 to Mullis).

In the initial studies with polymerase chain reaction (PCR), the DNA polymerase was added at the start of each round of DNA replication (see U.S. Pat. No. 4,683,202, supra). Subsequently, it was determined that thermostable DNA polymerases could be obtained from bacteria that grow at elevated temperatures, and that these enzymes need to be added only once (see U.S. Pat. No. 4,889,818 to Gelfand and U.S. Pat. No. 4,965,188 to Mullis). At the elevated temperatures used during PCR, these enzymes are not irreversibly inactivated. As a result, one can carry out repetitive cycles of polymerase chain reactions without adding fresh enzymes at the start of each synthetic addition process. DNA polymerases, particularly thermostable polymerases, are the key to a large number of techniques in recombinant DNA studies and in medical diagnosis of disease. For diagnostic applications in particular, a target nucleic acid sequence may be only a small portion of the DNA or RNA in question, so it may be difficult to detect the presence of a target nucleic acid sequence without amplification.

The overall folding pattern of polymerases resembles the human right hand and contains three distinct subdomains of palm, fingers, and thumb. (See Beese et al., *Science* 260:352-355, 1993); Patel et al., *Biochemistry* 34:5351-5363, 1995). While the structure of the fingers and thumb subdomains vary greatly between polymerases that differ in size and in cellular functions, the catalytic palm subdomains are all superimposable. For example, motif A, which interacts with the incoming dNTP and stabilizes the transition state during chemical catalysis, is superimposable with a mean deviation of about one Å amongst mammalian pol α and prokaryotic pol I family DNA polymerases (Wang et al., *Cell* 89:1087-1099, 1997). Motif A begins structurally at an antiparallel β-strand containing predominantly hydrophobic residues and continues to an α-helix. The primary amino acid sequence of DNA polymerase active sites is exceptionally conserved. In the case of motif A, for example, the sequence DYSQIELR (SEQ ID NO:30) is retained in polymerases from organisms separated by many millions years of evolution, including, e.g., *Thermus aquaticus, Chlamydia trachomatis*, and *Escherichia coli*. Taken together, these observations indicate that polymerases function by similar catalytic mechanisms.

In addition to being well-conserved, the active site of DNA polymerases has also been shown to be relatively mutable, capable of accommodating certain amino acid substitutions without reducing DNA polymerase activity significantly. (See, e.g., U.S. Pat. No. 6,602,695 to Patel et al.) Such mutant DNA polymerases can offer various selective advantages in, e.g., diagnostic and research applications comprising nucleic acid synthesis reactions. The present invention, as set forth herein, meets these and other needs.

BRIEF SUMMARY OF THE INVENTION

The present invention provides DNA polymerases having improved enzyme activity relative to the corresponding unmodified polymerase and which is useful in a variety of nucleic acid synthesis applications. In some embodiments, the polymerases are isolated or purified. In some embodiments, the DNA polymerase comprises the amino acid sequence $A-G-X_1-X_2-F-X_3-X_4-X_5-S-X_6-X_7-Q-X_8-X_9-X_{10}-X_{11}-L-X_{12}-X_{13}-X_{14}-X_{15}$ (SEQ ID NO:1) wherein $X_2, X_5, X_6, X_9$, and $X_{10}$ are any amino acid,
$X_1$ is H, E or Q,
$X_3$ is N or H,
$X_4$ is L or I,
$X_7$ is D, K or T,
$X_8$ is L or V,
$X_{11}$ is V, I or L,
$X_{12}$ is F or Y,
$X_{13}$ is an amino acid other than D or E,
$X_{14}$ is K or E, and
$X_{15}$ is L or Q;

wherein the polymerase has an improved nucleic acid extension rate relative to an otherwise identical DNA polymerase where $X_{13}$ is D or E. $X_2, X_5, X_6, X_9$, and $X_{10}$ can be any amino acid. In some embodiments, the mutant polymerase has G at position $X_{13}$. In some embodiments, the mutant polymerase has R or K at position $X_{13}$. In some embodiments, $X_2$ is selected from the group consisting of P, A, E, T, and V. In some embodiments, $X_5$ is selected from the group consisting of N, R, G, and S. In some embodiments, $X_6$ is selected from the group consisting of R, P, S, and T. In some embodiments, $X_9$ is selected from the group consisting of E, G, Q, S, and A. In some embodiments, $X_{10}$ is selected from the group consisting of R, T, A, V, Y, S and N. In some embodiments, $X_{13}$ is selected from A, C, F, G, H, I, K, L, M, N, P, Q, R, S, T, V, W, or Y.

In some embodiments, the DNA polymerases of the invention are modified versions of an unmodified polymerase. In its unmodified form, the polymerase is generally functional, having nucleotide-incorporating activity, and includes an amino acid sequence having the following motif in the polymerase domain:

$A-G-X_1-X_2-F-X_3-X_4-X_5-S-X_6-X_7-Q-X_8-X_9-X_{10}-X_{11}-L-X_{12}-X_{13}-X_{14}-X_{15}$ (SEQ ID NO:29); wherein $X_2, X_5, X_6, X_9$, and $X_{10}$ are any amino acid; $X_1$ is H, E or Q; $X_3$ is N or H; $X_4$ is L or I; $X_7$ is D, K or T; $X_8$ is L or V; $X_{11}$ is V, I or L; $X_{12}$ is F or Y; $X_{13}$ is D or E; $X_{14}$ is K or E; $X_{15}$ is L or Q.

The mutant polymerase (i.e., modified from SEQ ID NO:29) is further characterized in that it includes an amino acid substitution, relative to its unmodified form, at least at position $X_{13}$; and has an improved nucleic acid extension rate relative to its unmodified form. In some embodiments, the mutant polymerase has an amino acid other than D or E at position $X_{13}$. In some embodiments, the mutant polymerase has G at position $X_{13}$. In some embodiments, the mutant polymerase has R or K at position $X_{13}$.

Various DNA polymerases are amenable to mutation according to the present invention. Particularly suitable are thermostable polymerases, including wild-type or naturally occurring thermostable polymerases from various species of thermophilic bacteria, as well as thermostable polymerases derived from such wild-type or naturally occurring enzymes by amino acid substitution, insertion, or deletion, or other modification. Exemplary unmodified forms of polymerase include, e.g., CS5 or CS6 DNA polymerase, or a functional DNA polymerase having at least 80%, 85%, 90% or 95% sequence identity thereto. Other unmodified polymerases include, e.g., DNA polymerases from any of the following species of thermophilic bacteria (or a functional DNA polymerase having at least 90% sequence identity to such a polymerase): *Thermotoga maritima; Thermus aquaticus; Thermus thermophilus; Thermus flavus; Thermus filiformis; Thermus* sp. sps17; *Thermus* sp. Z05; *Thermotoga neopolitana; Thermosipho africanus; Thermus caldophilus* or *Bacillus caldotenax*. Suitable polymerases also include those having reverse transcriptase (RT) activity and/or the ability to incorporate unconventional nucleotides, such as ribonucleotides or other 2'-modified nucleotides.

In some embodiments, the unmodified form of the polymerase comprises a chimeric polymerase. In one embodiment, for example, the unmodified form of the chimeric polymerase is CS5 DNA polymerase (SEQ ID NO:20), CS6 DNA polymerase (SEQ ID NO:21), or a polymerase having at least 90% sequence identity to the CS5 DNA polymerase or the CS6 DNA polymerase. In specific variations, the unmodified form of the chimeric polymerase includes one or more amino acid substitutions relative to SEQ ID NO:20 or SEQ ID NO:21 that are selected from G46E, L329A, and E678G. For example, the unmodified form of the mutant polymerase can be G46E CS5; G46E L329A CS5; G46E E678G CS5; or G46E L329A E678G CS5. In exemplary embodiments, these unmodified forms are substituted to provide a mutant polymerase with a E558G substitution. For example, the mutant DNA polymerase can be any one of the following: G46E E558G CS5; G46E L329A E558G CS5; G46E E558G E678G CS5; G46E L329A E558G E678G CS5; or the like. In some embodiments, the unmodified form of the chimeric polymerase includes one or more amino acid substitutions relative to SEQ ID NO:20 or SEQ ID NO:21 that are selected from S671F, D640G, Q601R, and I669F. For example, the unmodified form of the mutant polymerase can be S671F CS5; D640G CS5; Q601R CS5; I669F CS5; S671F D640G CS5; S671F Q601R CS5; S671F I669F CS5; D640G Q601R CS5; D640G I669F CS5; Q601R I669F CS5; S671F D640G Q601R CS5; S671F D640G I669F CS5; S671F Q601R I669F CS5; D640G Q601R I669F CS5; or S671F D640G Q601R I669F CS5. In exemplary embodiments, these unmodified forms are substituted to provide a mutant polymerase with a E558G substitutions. For example, the mutant DNA polymerase can be any one of the following: E558G S671F CS5; E558G D640G CS5; E558G Q601R CS5; E558G I669F CS5; E558G S671F D640G CS5; E558G S671F Q601R CS5; E558G S671F I669F CS5; E558G D640G Q601R CS5; E558G D640G I669F CS5; E558G Q601R I669F CS5; E558G S671F D640G Q601R CS5; E558G S671F D640G I669F CS5; E558G S671F Q601R I669F CS5; E558G D640G Q601R I669F CS5; E558G S671F D640G Q601R I669F CS5; or the like. In some embodiments, the unmodified form of the chimeric polymerase includes one or more amino acid substitutions relative to SEQ ID NO:20 or SEQ ID NO:21 that are selected from G46E, L329A, and E678G, and further includes one or more amino acid substitutions relative to SEQ ID NO:20 or SEQ ID NO:21 that are selected from S671F, D640G, Q601R, and I669F. For example, the unmodified form of the mutant polymerase can be G46E L329A S671F E678G CS5; or the like. In exemplary embodiments, these unmodified forms are substituted to provide a mutant polymerase with a E558G substitutions. For example, the mutant DNA polymerase can be E558G G46E L329A S671F E678G CS5 or the like.

The DNA polymerase enzyme activity can be further improved with other, non-substitutional modifications. One such modification is a thermally reversible covalent modification that inactivates the enzyme, but which is reversed to activate the enzyme upon incubation at an elevated temperature, such as a temperature typically used for primer extension. In one embodiment, the DNA polymerase comprising the thermally reversible covalent modification is produced by a reaction, carried out at alkaline pH at a temperature that is less than about 25° C., of a mixture of a thermostable DNA polymerase and a dicarboxylic acid anhydride having one of the following formulas I or II:

wherein $R_1$ and $R_2$ are hydrogen or organic radicals, which may be linked; or

wherein $R_1$ and $R_2$ are organic radicals, which may linked, and the hydrogens are cis. In a specific variation of such an enzyme, the unmodified form of the polymerase is G64E CS5.

In various other aspects, the present invention provides a recombinant nucleic acid encoding a DNA polymerase as described herein, a vector comprising the recombinant nucleic acid, and a host cell transformed with the vector. In certain embodiments, the vector is an expression vector. Host cells comprising such expression vectors are useful in methods of the invention for producing the polymerase by culturing the host cells under conditions suitable for expression of the recombinant nucleic acid.

In yet another aspect, a method for conducting primer extension is provided. The method generally includes contacting a DNA polymerase of the invention with a primer, a polynucleotide template, and free nucleotides under conditions suitable for extension of the primer, thereby producing an extended primer. The polynucleotide template can be, for example, an RNA or DNA template. The free nucleotides can include unconventional nucleotides such as, e.g., ribonucleotides and/or labeled nucleotides. Further, the primer and/or template can include one or more nucleotide analogs. In some variations, the primer extension method is a method for polynucleotide amplification that includes contacting a DNA polymerase of the invention with a primer pair, the polynucleotide template, and the free nucleotides under conditions suitable for amplification of the polynucleotide.

The present invention also provides a kit useful in such a primer extension method. Generally, the kit includes at least one container providing a DNA polymerase of the invention as described herein. In certain embodiments, the kit further includes one or more additional containers providing one or more additional reagents. For example, in specific variations, the one or more additional containers provide free nucleotides; a buffer suitable for primer extension; and/or a primer hybridizable, under primer extension conditions, to a predetermined polynucleotide template.

DEFINITIONS

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry*, $5^{th}$ ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," *Proc. Natl. Acad. Sci. U.S.A.* 101 (24):8882-8887, Anderson et al. (2004) "An expanded genetic code with a functional quadruplet codon" *Proc. Natl. Acad. Sci. U.S.A.* 101(20):7566-7571, Ikeda et al. (2003) "Synthesis of a novel histidine analogue and its efficient incorporation into a protein in vivo," *Protein Eng. Des. Sel.* 16(9):699-706, Chin et al. (2003) "An Expanded Eukaryotic Genetic Code," *Science* 301(5635):964-967, James et al. (2001) "Kinetic characterization of ribonuclease S mutants containing photoisomerizable phenylazophenylalanine residues," *Protein Eng. Des. Sel.* 14(12):983-991, Kohrer et al. (2001) "Import of amber and ochre suppressor tRNAs into mammalian cells: A general approach to site-specific insertion of amino acid analogues into proteins," *Proc. Natl. Acad. Sci. U.S.A.* 98(25):14310-14315, Bacher et al. (2001) "Selection and Characterization of *Escherichia coli* Variants Capable of Growth on an Otherwise Toxic Tryptophan Analogue," *J. Bacteriol.* 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," *J. Biol. Chem.* 275(51):40324-40328, and Budisa et al. (2001) "Proteins with {beta}-(thienopyrrolyl)alanines as alternative chromophores and pharmaceutically active amino acids," *Protein Sci.* 10(7): 1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "mutant," in the context of DNA polymerases of the present invention, means a polypeptide, typically recombinant, that comprises one or more amino acid substitutions relative to a corresponding, functional DNA polymerase.

The term "unmodified form," in the context of a mutant polymerase, is a term used herein for purposes of defining a mutant DNA polymerase of the present invention: the term "unmodified form" refers to a functional DNA polymerase that has the amino acid sequence of the mutant polymerase except at one or more amino acid position(s) specified as characterizing the mutant polymerase. Thus, reference to a mutant DNA polymerase in terms of (a) its unmodified form and (b) one or more specified amino acid substitutions means that, with the exception of the specified amino acid substitution(s), the mutant polymerase otherwise has an amino acid sequence identical to the unmodified form in the specified motif. The polymerase may contain additional mutations to provide desired functionality, e.g., improved incorporation of dideoxyribonucleotides, ribonucleotides, ribonucleotide analogs, dye-labeled nucleotides, modulating 5'-nuclease activity, modulating 3'-nuclease (or proofreading) activity, or the like. Accordingly, in carrying out the present invention as described herein, the unmodified form of a DNA polymerase is predetermined. The unmodified form of a DNA polymerase can be, for example, a wild-type and/or a naturally occurring DNA polymerase, or a DNA polymerase that has already been intentionally modified. An unmodified form of the polymerase is preferably a thermostable DNA polymerases, such as DNA polymerases from various thermophilic bacteria, as well as functional variants thereof having substantial sequence identity to a wild-type or naturally occurring thermostable polymerase Such variants can include, for example, chimeric DNA polymerases such as, for example, the chimeric DNA polymerases described in U.S. Pat. No. 6,228,628 and U.S. Application Publication No. 2004/0005599, which are incorporated by reference herein in their entirety. In certain embodiments, the unmodified form of a polymerase has reverse transcriptase (RT) activity.

The term "thermostable polymerase," refers to an enzyme that is stable to heat, is heat resistant, and retains sufficient activity to effect subsequent primer extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form primer extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species sps17, *Thermus* species Z05, *Thermus caldophilus, Bacillus caldotenax, Thermotoga neopolitana*, and *Thermosipho africanus*.

As used herein, a "chimeric" protein refers to a protein whose amino acid sequence represents a fusion product of subsequences of the amino acid sequences from at least two distinct proteins. A chimeric protein typically is not produced by direct manipulation of amino acid sequences, but, rather, is expressed from a "chimeric" gene that encodes the chimeric amino acid sequence. In certain embodiments, for example, an unmodified form of a mutant DNA polymerase of the present invention is a chimeric protein that consists of an amino-terminal (N-terminal) region derived from a *Thermus* species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus.

In the context of mutant DNA polymerases, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified DNA polymerase represents referral to a collection of equivalent positions in other recognized DNA polymerases and structural homologues and families. In typical embodiments of the present invention, "correspondence" of amino acid positions are determined with respect to a region of the polymerase comprising the motif of SEQ ID NO: 1, as discussed further herein.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above. A recombinant protein is typically distinguished from naturally occurring protein by at least one or more characteristics.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981); automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

The term "primer" as used herein refers to a polynucleotide capable of acting as a point of initiation of template-directed nucleic acid synthesis when placed under conditions in which primer extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in ELISA assays), biotin, or haptens and proteins for which antisera or monoclonal antibodies are available.

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively, these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs. Additional examples of terminator compounds include 2'-PO$_4$ analogs of ribonucleotides (see, e.g., U.S. Application Publication Nos. 2005/0037991 and 2005/0037398, which are both incorporated by reference). Other unconventional nucleotides include phosphorothioate dNTPs ([[α]-S]dNTPs), 5'-[α]-borano-dNTPs, [α]-methyl-phosphonate dNTPs, and ribonucleoside triphosphates (rNTPs). Unconventional bases may be labeled with radioactive isotopes such as $^{32}$P, $^{33}$P, or $^{35}$S; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, Mass.), Applied Biosystems (Foster City, Calif.), or Invitrogen/Molecular Probes (Eugene, Oreg.). Dyes of the cyanine family include Cy2, Cy3, Cy5, and Cy7 and are marketed by GE Healthcare UK Limited (Amersham Place, Little Chalfont, Buckinghamshire, England).

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance.

For example, a nucleic acid is considered similar to a reference sequence if the smallest sum probability in a comparison of the test nucleic acid to the reference nucleic acid is less than about 0.2, typically less than about 0.01, and more typically less than about 0.001.

The term "nucleic acid extension rate" refers the rate at which a biocatalyst (e.g., an enzyme, such as a polymerase, ligase, or the like) extends a nucleic acid (e.g., a primer or other oligonucleotide) in a template-dependent or template-independent manner by attaching (e.g., covalently) one or more nucleotides to the nucleic acid. To illustrate, certain mutant DNA polymerases described herein have improved nucleic acid extension rates relative to unmodified forms of these DNA polymerases, such that they can extend primers at higher rates than these unmodified forms under a given set of reaction conditions.

The term "reverse transcription efficiency" refers to the fraction of RNA molecules that are reverse transcribed as cDNA in a given reverse transcription reaction.

BRIEF DESCRIPTION OF THE DRAWINGS

FIG. 1 depicts an amino acid sequence alignment of a region from the polymerase domain of exemplary thermostable DNA polymerases from various species of thermophilic bacteria and Bacteriophage T7: *Thermus thermophilus* (Tth) (SEQ ID NO:3), *Thermus caldophilus* (Tca) (SEQ ID NO:4), *Thermus* sp. Z05 (Z05) (SEQ ID NO:5), *Thermus aquaticus* (Taq) (SEQ ID NO:6), *Thermus flavus* (Tfl) (SEQ ID NO:7), *Thermus filiformis* (Tfi) (SEQ ID NO:8), *Thermus* sp. sps17 (Sps17) (SEQ ID NO:9), *Deinococcus radiodurans* (Dra) (SEQ ID NO:10), Hot Spring family B/clone 7 (HspB) (SEQ ID NO:11), *Bacillus stearothermophilus* (Bst) (SEQ ID NO:12), *Bacillus caldotenax* (Bca) (SEQ ID NO:13), *Escherchia coli* (Eco) (SEQ ID NO:14), *Thermotoga maritime* (Tma) (SEQ ID NO:15), *Thermotoga neapolitana* (Tne) (SEQ ID NO:16), *Thermosipho africanus* (Taf) (SEQ ID NO:17), Hot Spring family A (HspA) (SEQ ID NO:18), and Bacteriophage T7 (T7) (SEQ ID NO:19). The amino acid sequence alignment also includes a region (SEQ ID NOS:31 and 32) from the polymerase domain of representative chimeric thermostable DNA polymerases, namely, CS5 and CS6. In addition, a sequence (Cons) (SEQ ID NO:24) showing consensus amino acid residues among these exemplary sequences is also included. Further, the polypeptide regions shown comprise the amino acid motif AGXXFXXXSXX-QXXXXLXXXX (SEQ ID NO: 1), the variable positions of which are further defined herein. These motifs are highlighted in bold type for CS5 and CS6 polymerase sequences. The amino acid position amenable to mutation in accordance with the present invention is indicated with an asterisk (*). Gaps in the alignments are indicated with a dot (.).

FIG. 2A presents the amino acid sequence of the chimeric thermostable DNA polymerase CS5 (SEQ ID NO:20).

FIG. 2B presents a nucleic acid sequence encoding the chimeric thermostable DNA polymerase CS5 (SEQ ID NO:22).

FIG. 3A presents the amino acid sequence of the chimeric thermostable DNA polymerase CS6 (SEQ ID NO:21).

FIG. 3B presents a nucleic acid sequence encoding the chimeric thermostable DNA polymerase CS6 (SEQ ID NO:23).

DETAILED DESCRIPTION

Figure 4:
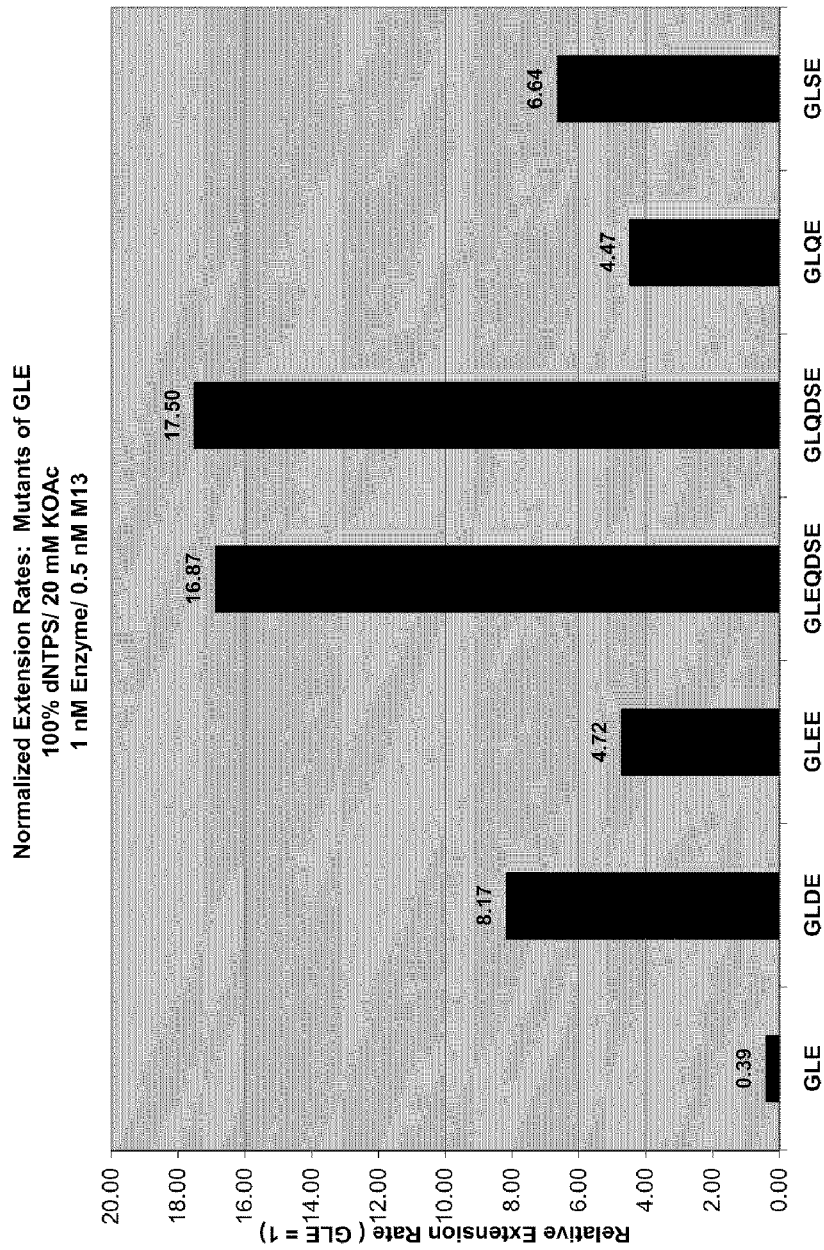
FIG. 4 is a bar graph that shows the normalized extension rates of various mutants of a G46E L329A E678G (GLE) CS5 DNA polymerase. The y-axis represents the relative extension rates, while the x-axis represents the DNA polymerases having specified point mutations (GLE=G46E L329A E678G CS5 DNA polymerase, GLDE=G46E L329A D640G E678G CS5 DNA polymerase, GLEE=G46E L329A E558G E678G CS5 DNA polymerase, GLEQDSE=G46E L329A E558G Q601R D640G S671F E678G CS5 DNA polymerase, GLQDSE=G46E L329A Q601R D640G S671F E678G CS5 DNA polymerase, GLQE=G46E L329A Q601R E678G CS5 DNA polymerase, GLSE=G46E L329A S671F E678G CS5 DNA polymerase). The extension rate values obtained for the mutant polymerases are normalized relative to the value obtained for the GLE CS5 DNA polymerase, which is set to 1.00.

The present invention provides novel DNA polymerases having improved rates of primer extension. The DNA polymerases of the invention may be used at lower concentrations for superior or equivalent performance as the parent enzymes. In view of similar activities of other mutants previously identified, it is expected that the DNA polymerases of the present invention in certain embodiments will have concomitant increases in reverse transcriptase activity and/or amplification activity. The DNA polymerases of the invention are therefore useful in a variety of applications involving primer extension as well as reverse transcription or amplification of polynucleotide templates, including, for example, applications in recombinant DNA studies and medical diagnosis of disease.

In some embodiments of the invention, the DNA polymerases of the invention comprise the following amino acid motif:

Ala-Gly-$X_{aa}$-$X_{aa}$-Phe-$X_{aa}$-$X_{aa}$-$X_{aa}$-Ser-$X_{aa}$-$X_{aa}$-Gln-$X_{aa}$-$X_{aa}$-$X_{aa}$-$X_{aa}$-Leu-$X_{aa}$-$X_{aa}$-$X_{aa}$-$X_{aa}$ (also referred to herein in the one-letter code as A-G-$X_1$-$X_2$-F-$X_3$-$X_4$-$X_5$-S-$X_6$-$X_7$-Q-$X_8$-$X_9$-$X_{10}$-$X_{11}$-L-$X_{12}$-$X_{13}$-$X_{14}$-$X_{15}$ (SEQ ID NO:1)); wherein $X_2$, $X_5$, $X_6$, $X_9$, and $X_{10}$ are any amino acid;
$X_1$ is His (H), Glu (E) or Gln (Q);
$X_3$ is Asn (N) or His (H);
$X_4$ is Leu (L) or Ile (I);
$X_7$ is Asp (D), Lys (K) or Thr (T);
$X_8$ is Leu (L) or Val (V);
$X_{11}$ is Val (V), Ile (I) or Leu (L);
$X_{12}$ is Phe (F) or Tyr (Y);
$X_{13}$ is an amino acid other than Asp (D) or Glu (E);
$X_{14}$ is Lys (K) or Glu (E); and
$X_{15}$ is Leu (L) or Gln (Q).

wherein the polymerase has an improved nucleic acid extension rate relative to an otherwise identical DNA polymerase where $X_{13}$ is D or E. In some embodiments, $X_{13}$ is G. In some embodiments, $X_{13}$ is A, C, F, H, I, K, L, M, N, P, Q, R, S, T, V, W, or Y.

In some embodiments of SEQ ID NO:1, $X_2$, $X_5$, $X_6$, $X_9$, and $X_{10}$ are any amino acids found in corresponding positions in any DNA polymerase. Exemplary DNA polymerases include those from *Thermus thermophilus, Thermus caldophilus, Thermus* sp. Z05, *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Escherchia coli, Thermotoga maritima, Thermotoga neapolitana, Thermosipho africanus*, Hot Spring family A, and Bacteriophage T7. In some embodiments, $X_2$ is selected from the group consisting of Pro (P), Ala (A), Glu (E), Thr (T), and Val (V). In some embodiments, $X_5$ is selected from the group consisting of Asn (N), Arg (R), Gly (G), and Ser (S). In some embodiments, $X_6$ is selected from the group consisting of Arg (R), Pro (P), Ser (S), and Thr (T).

In some embodiments, $X_9$ is selected from the group consisting of Glu (E), Gly (G), Gln (Q), Ser (S), and Ala (A). In some embodiments, $X_{10}$ is selected from the group consisting of Arg (R), Thr (T), Ala (A), Val (V), Tyr (Y), Ser (S) and Asn (N).

In some embodiments of the invention, the DNA polymerase of the invention comprises the following amino acid motif:

$X_{aa}$-$X_{aa}$-$X_{aa}$-$X_{aa}$-Phe-$X_{aa}$-$X_{aa}$-$X_{aa}$-Ser-$X_{aa}$-$X_{aa}$-$X_{aa}$-$X_{aa}$-$X_{aa}$-$X_{aa}$-$X_{aa}$-Leu-$X_{aa}$-$X_{aa}$-$X_{aa}$-$X_{aa}$ (also referred to herein in the one-letter code as $T_1$-$T_2$-$X_1$-$X_2$-F-$X_3$-$X_4$-$X_5$-S-$X_6$-$X_7$-$T_3$-$X_8$-$X_9$-$X_{10}$-$X_{11}$-L-$X_{12}$-$X_{13}$-$X_{14}$-$X_{15}$ (SEQ ID NO:2)); wherein $T_1$ is Ala (A) or Val (V);
$T_2$ is Gly (G) or Val (V);
$T_3$ is Gln (L) or H is (H);
$X_2$, $X_5$, $X_6$, $X_9$, and $X_{10}$ are any amino acid or absent;
$X_1$ is His (H), Glu (E), Gln (Q) or absent;
$X_3$ is Asn (N) or His (H);
$X_4$ is Leu (L), Ile (I) or Pro (P);
$X_7$ is Asp (D), Lys (K) or Thr (T);
$X_8$ is Leu (L), Val (V) or Ile (I);
$X_{11}$ is Val (V), Ile (I), Leu (L) or Lys (K);
$X_{12}$ is Phe (F), Tyr (Y) or Gln (Q);
$X_{13}$ is an amino acid other than Asp (D) or Glu (E);
$X_{14}$ is Lys (K), Glu (E) or Ala (A); and
$X_{15}$ is Leu (L), Gln (Q) or Gly (G).

wherein the polymerase has an improved nucleic acid extension rate relative to an otherwise identical DNA polymerase where $X_{13}$ is D or E. In some embodiments, $X_{13}$ is G. The above motif (SEQ ID NO:2) was generated by alignment of all of the sequences displayed in FIG. 1, whereas the motif displayed in SEQ ID NO: 1 was generated by alignment of all of the sequences displayed in FIG. 1 except for T7 DNA polymerase amino acid residues.

In some embodiments of SEQ ID NO:2, $X_2$, $X_5$, $X_6$, $X_9$, and $X_{10}$ are any amino acids found in corresponding positions in any DNA polymerase, e.g. DNA polymerases from *Thermus thermophilus, Thermus caldophilus, Thermus* sp. Z05, *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Escherchia coli, Thermotoga maritima, Thermotoga neapolitana, Thermosipho africanus*, Hot Spring family A, and Bacteriophage T7. In some embodiments, $X_2$ is selected from the group consisting of P, A, E, T, and V, or is absent; $X_5$ is selected from the group consisting of N, R, G, and S; $X_6$ is selected from the group consisting of R, P, S, and T; $X_9$ is selected from the group consisting of E, G, Q, S, and A; and $X_{10}$ is selected from the group consisting of R, T, A, V, Y, S, N and K.

As discussed above, $X_2$, $X_5$, $X_6$, $X_9$, and $X_{10}$ can be any amino acid. In some embodiments, $X_2$ is selected from the group consisting of Pro (P), Ala (A), Glu (E), Thr (T), and Val (V). In some embodiments, $X_5$ is selected from the group consisting of Asn (N), Arg (R), Gly (G), and Ser (S). In some embodiments, $X_6$ is selected from the group consisting of Arg (R), Pro (P), Ser (S), and Thr (T). In some embodiments, $X_9$ is selected from the group consisting of Glu (E), Gly (G), Gln (Q), Ser (S), and Ala (A). In some embodiments, $X_{10}$ is selected from the group consisting of Arg (R), Thr (T), Ala (A), Val (V), Tyr (Y), Ser (S) and Asn (N).

Unmodified forms of DNA polymerases amenable to mutation in accordance with the present invention are those having a functional polymerase domain comprising the following amino acid motif:

Ala-Gly-$X_{aa}$-$X_{aa}$-Phe-$X_{aa}$-$X_{aa}$-$X_{aa}$-Ser-$X_{aa}$-$X_{aa}$-Gln-$X_{aa}$-$X_{aa}$-$X_{aa}$-$X_{aa}$-Leu-$X_{aa}$-$X_{aa}$-$X_{aa}$-$X_{aa}$ (also referred to herein in the one-letter code as A-G-$X_1$-$X_2$-F-$X_3$-$X_4$-$X_5$-S-$X_6$-$X_7$-Q-$X_8$-$X_9$-$X_{10}$-$X_{11}$-L-$X_{12}$-$X_{13}$-$X_{14}$-$X_{15}$ (SEQ ID NO:29)); wherein $X_2$, $X_5$, $X_6$, $X_9$, and $X_{10}$ are any amino acid;
$X_1$ is His (H), Glu (E) or Gln (Q);
$X_3$ is Asn (N) or His (H);
$X_4$ is Leu (L) or Ile (I);
$X_7$ is Asp (D), Lys (K) or Thr (T);
$X_8$ is Leu (L) or Val (V);
$X_{11}$ is Val (V), Ile (I) or Leu (L);
$X_{12}$ is Phe (F) or Tyr (Y);
$X_{13}$ is Asp (D) or Glu (E);
$X_{14}$ is Lys (K) or Glu (E); and
$X_{15}$ is Leu (L) or Gln (Q).

The motif presented above (SEQ ID NO:29) is present within the thumb subdomain in the active site of many Family A type DNA-dependent DNA polymerases, particularly thermostable DNA polymerases from thermophilic bacteria and Bacteriophage T7. For example, FIG. 1 shows an amino acid sequence alignment of a region from the polymerase domain of DNA polymerases from several species of bacteria: *Thermus thermophilus, Thermus caldophilus, Thermus* sp. Z05, *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Escherchia coli, Thermotoga maritima, Thermotoga neapolitana, Thermosipho africanus*, Hot Spring family A, and Bacteriophage T7. The amino acid sequence alignment shown in FIG. 1 also includes a region from the polymerase domain of representative chimeric thermostable DNA polymerases. As shown, the motif of SEQ ID NO:29 is present in each of these polymerases, indicating a conserved function for this region of the active site.

Accordingly, in some embodiments, the unmodified form of the DNA polymerase is a wild-type or a naturally occurring DNA polymerase, such as, for example, a polymerase from any of the species of bacteria listed above. In one variation, the unmodified polymerase is from a species of the genus *Thermus*. In other embodiments of the invention, the unmodified polymerase is from a thermophilic species other than *Thermus*. The full nucleic acid and amino acid sequence for numerous thermostable DNA polymerases are available. The sequences each of *Thermus aquaticus* (Taq), *Thermus thermophilus* (Tth), *Thermus* species Z05, *Thermus* species sps17, *Thermotoga maritima* (Tma), and *Thermosipho africanus* (Taf) polymerase have been published in PCT International Patent Publication No. WO 92/06200, which is incorporated herein by reference. The sequence for the DNA polymerase from *Thermus flavus* has been published in Akhmetzjanov and Vakhitov (*Nucleic Acids Research* 20:5839, 1992), which is incorporated herein by reference. The sequence of the thermostable DNA polymerase from *Thermus caldophilus* is found in EMBL/GenBank Accession No. U62584. The sequence of the thermostable DNA polymerase from *Thermus filiformis* can be recovered from ATCC Deposit No. 42380 using, e.g., the methods provided in U.S. Pat. No. 4,889,818, as well as the sequence information provided therein. The sequence of the *Thermotoga neapolitana* DNA polymerase is from GeneSeq Patent Data Base Accession No. R98144 and PCT WO 97/09451, each incorporated herein by reference. The sequence of the thermostable DNA polymerase from *Bacillus caldotenax* is described in, e.g., Uemori et al. (*J Biochem* (*Tokyo*) 113(3):401-410, 1993; see also, Swiss-Prot database Accession No. Q04957 and GenBank Accession Nos. D12982 and BAA02361), which are each incorporated by reference. The sequence for the DNA polymerase from *Bacillus stearothermophilus* has been published in U.S. Pat. No. 6,066,483, which is incorporated herein by reference. Examples of unmodified forms of DNA polymerases that can be modified as described herein are also described in, e.g., U.S. Pat. No. 6,228,628, entitled "Mutant chimeric DNA polymerase" issued May 8, 2001 to Gelfand et al.; U.S. Pat. No. 6,346,379, entitled "Thermostable DNA polymerases incorporating nucleoside triphosphates labeled with fluorescein family dyes" issued Feb. 12, 2002 to Gelfand et al.; U.S. Pat. No. 7,030,220, entitled "Thermostable enzyme promoting the fidelity of thermostable DNA polymerases-for improvement of nucleic acid synthesis and amplification in vitro" issued Apr. 18, 2006 to Ankenbauer et al.; U.S. Pat. No. 6,881,559, entitled "Mutant B-type DNA polymerases exhibiting improved performance in PCR" issued Apr. 19, 2005 to Sobek et al.; U.S. Pat. No. 6,794,177, entitled "Modified DNA-polymerase from carboxydothermus hydrogenoformans and its use for coupled reverse transcription and polymerase chain reaction" issued Sep. 21, 2004 to Markau et al.; U.S. Pat. No. 6,468,775, entitled "Thermostable DNA polymerase from carboxydothermus hydrogenoformans" issued Oct. 22, 2002 to Ankenbauer et al.; and U.S. Pat. Appl. Nos. 20040005599, entitled "Thermostable or thermoactive DNA polymerase molecules with attenuated 3'-5' exonuclease activity" filed Mar. 26, 2003 by Schoenbrunner et al.; 20020012970, entitled "High temperature reverse transcription using mutant DNA polymerases" filed Mar. 30, 2001 by Smith et al.; 20060078928, entitled "Thermostable enzyme promoting the fidelity of thermostable DNA polymerases-for improvement of nucleic acid synthesis and amplification in vitro" filed Sep. 29, 2005 by Ankenbauer et al.; 20040115639, entitled "Reversibly modified thermostable enzymes for DNA synthesis and amplification in vitro" filed Dec. 11, 2002 by Sobek et al., which are each incorporated by reference.

Also amenable to the mutations described herein are functional DNA polymerases that have been previously modified (e.g., by amino acid substitution, addition, or deletion), provided that the previously modified polymerase retains the amino acid motif of SEQ ID NO:1. Thus, suitable unmodified DNA polymerases also include functional variants of wild-type or naturally occurring polymerases. Such variants typically will have substantial sequence identity or similarity to the wild-type or naturally occurring polymerase, typically at least 80% sequence identity and more typically at least 90%, 95%, or 98% sequence identity. In certain embodiments, the unmodified DNA polymerase has reverse transcriptase (RT) activity and/or the ability to incorporate ribonucleotides or other 2'-modified nucleotides.

Suitable polymerases also include, for example, certain chimeric DNA polymerases comprising polypeptide regions from two or more enzymes. Examples of such chimeric DNA polymerases are described in, e.g., U.S. Pat. No. 6,228,628, which is incorporated by reference herein in its entirety. Particularly suitable are chimeric CS-family DNA polymerases, which include the CS5 (SEQ ID NO:20) and CS6 (SEQ ID NO:21) polymerases and variants thereof having substantial sequence identity or similarity to SEQ ID NO:20 or SEQ ID NO:21 (typically at least 80% sequence identity and more typically at least 90% sequence identity). The CS5 and CS6 DNA polymerases are chimeric enzymes derived from *Thermus* sp. Z05 and *Thermotoga maritima* (Tma) DNA polymerases. They comprise the N-terminal 5'-nuclease domain of the *Thermus enzyme* and the C-terminal 3'-5' exonuclease and the polymerase domains of the Tma enzyme. These enzymes have efficient reverse transcriptase activity, can extend nucleotide analog-containing primers, and can incorporate alpha-phosphorothioate dNTPs, dUTP, dITP, and also fluorescein- and cyanine-dye family labeled dNTPs. The CS5 and CS6 polymerases are also efficient $Mg^{2+}$-activated PCR enzymes. Nucleic acid sequences encoding CS5 and CS6 polymerases are provided in FIGS. 2B and 3B, respectively. CS5 and CS6 chimeric polymerases are further described in, e.g., U.S. Pat. Application Publication No. 2004/0005599, which is incorporated by reference herein in its entirety.

In some embodiments, the unmodified form of the DNA polymerase is a polymerase that has been previously modified, typically by recombinant means, to confer some selective advantage. Such modifications include, for example, the amino acid substitutions G46E, L329A, and/or E678G in CS5 DNA polymerase, CS6 DNA polymerase, or corresponding mutation(s) in other polymerases. Accordingly, in specific variations, the unmodified form of the DNA polymerase is one of the following (each having the amino acid sequence of SEQ ID NO:20 or SEQ ID NO:21 except for the designated substitution(s)): G46E; G46E L329A; G46E E678G; or G46E L329A E678G. The E678G substitution, for example, allows for the incorporation of ribonucleotides and other 2'-modified nucleotides, but this mutation also appears to result in an impaired ability to extend primed templates. In certain embodiments, the mutations according to the present invention, which result in a faster extension rate of the mutant polymerase, ameliorate the E678G mutation's impaired ability to extend primed templates.

The mutant DNA polymerases of the present invention comprise one or more amino acid substitutions relative to the unmodified polymerase, i.e. at position $X_{13}$ of SEQ ID NO: 1. Amino acid substitution at this position confers improved nucleotide-incorporating activity, yielding a DNA polymerase with an improved (faster) nucleic acid extension rate relative to the corresponding DNA polymerase that is otherwise identical but includes an E or D at position $X_{13}$. While not intending to be limited to any particular theory, the present inventors believe that the improved nucleic acid extension rate of the mutant polymerases of the invention is a consequence of tighter binding to a template, i.e., less frequent dissociation from the template, resulting in a higher "processivity" enzyme. These features permit using lower concentrations of the mutant polymerase in, e.g., primer extension reactions relative to reactions involving the unmodified DNA polymerase. Thus, at a sufficiently high enzyme concentration, the extension rate of the unmodified polymerase (i.e., lacking the specific mutations that are the subject of the invention) could conceivably approach that of the mutant enzyme. The mutant polymerases also is expected to perform much better than the unmodified forms at high ionic strength. However, at a sufficiently high enzyme concentration, the performance of the unmodified polymerase at low ionic strength would approach that of the mutant polymerase.

Because the unmodified forms of DNA polymerase are unique, the amino acid position corresponding to $X_{13}$ is typically distinct for each mutant polymerase. Amino acid and nucleic acid sequence alignment programs are readily available (see, e.g., those referred to supra) and, given the particular motif identified herein, serve to assist in the identification of the exact amino acids (and corresponding codons) for modification in accordance with the present invention. The positions corresponding to $X_{13}$ are shown in Table 1 for representative chimeric thermostable DNA polymerases and thermostable DNA polymerases from exemplary thermophilic species.

TABLE 1

Amino Acid Positions Corresponding to Motif Positions $X_{13}$ in Exemplary Thermostable Polymerases.

| Organism or Chimeric Sequence Consensus | $X_{13}$ Position |
|---|---|
| T. thermophilus | 498 |
| T. caldophilus | 498 |
| T. sp. Z05 | 498 |
| T. aquaticus | 496 |
| T. flavus | 495 |
| T. filiformis | 494 |
| T. sp. sps17 | 494 |
| D. radiodurans | 586 |
| Hot Spring family B/clone 7 | 546 |
| B. stearothermophilus | 540 |
| B. caldotenax | 540 |
| E. coli | 592 |
| T. maritima | 558 |
| T. neapolitana | 558 |
| T. africanus | 558 |
| Hot Spring family A | 595 |
| CS5 | 558 |
| CS6 | 558 |

As previously discussed, in some embodiments, the mutant DNA polymerase of the present invention is derived from CS5 DNA polymerase (SEQ ID NO:20), CS6 DNA polymerase (SEQ ID NO:21), or a variant of those polymerases (e.g., G46E; G46E L329A; G46E E678G; G46E L329A E678G; or the like). As referred to above, in CS5 DNA polymerase or CS6 DNA polymerase, position $X_{13}$ corresponds to Glutamic acid (E) at position 558. Thus, in certain variations of the invention, the mutant polymerase comprises an amino acid substitution at position $X_{13}$, relative to a CS5 DNA polymerase or a CS6 DNA polymerase that is otherwise identical. Exemplary CS5 DNA polymerase and CS6 DNA polymerase mutants include those comprising the amino acid substitution(s) E558G. Other, exemplary CS5 DNA polymerase and CS6 DNA polymerase mutants include the following (each having the amino acid sequence of SEQ ID NO:20 or SEQ ID NO:21 except for the designated substitutions):

G46E E558G;
G46E L329A E558G;
G46E E558G E678G;
L329A E558G E678G; and
G46E L329A E558G E678G.

In some embodiments, the amino acid substitutions are single amino acid substitutions at position $X_{13}$. Alternatively, the mutant polymerase comprises the amino acid substitution at position $X_{13}$ in combination with the amino acid substitutions at other positions, particularly those amino acid substitutions that are known to improve the nucleic acid extension rate of the DNA polymerase, for example, amino acid substitutions (other than those residues shown below for $X_{a8}$) at position $X_{a8}$ of DNA polymerases having a functional polymerase domain comprising the following amino acid motif:

Xaa-Xaa-Xaa-Xaa-Arg-Xaa-Xaa-Xaa-Lys-Leu-Xaa-Xaa-Thr-Tyr-Xaa-Asp (also referred to herein in the one-letter code as $X_{a1}$-$X_{a2}$-$X_{a3}$-$X_{a4}$-R-$X_{a6}$-$X_{a7}$-$X_{a8}$-K-L-$X_{a11}$-$X_{a12}$-T-Y-$X_{a15}$-$X_{a16}$ (SEQ ID NO:25));
wherein
$X_{a1}$ is Ile (I) or Leu (L);
$X_{a2}$ is Gln (Q) or Leu (L);
$X_{a3}$ is Gln (Q), His (H) or Glu (E);
$X_{a4}$ is Tyr (Y), His (H), or Phe (F);
$X_{a6}$ is Glu (E), Gln (Q) or Lys (K);
$X_{a7}$ is Ile (I), Leu (L) or Tyr (Y);
$X_{a8}$ is Gln (Q), Thr (T), Met (M), Gly (G) or Leu (L);
$X_{a11}$ is Lys (K) or Gln (Q);
$X_{a12}$ is Ser (S) or Asn (N);
$X_{a15}$ is Ile (I) or Val (V); and
$X_{a16}$ is Glu (E) or Asp (D).

In some embodiments, the mutant polymerase comprises the amino acid substitution at position $X_{13}$ in combination with the amino acid substitutions (other than those residues shown below for $X_{b8}$) at position $X_{b8}$ of DNA polymerases having a functional polymerase domain comprising the following amino acid motif:

Thr-Gly-Arg-Leu-Ser-Ser-Xaa-Xaa-Pro-Asn-Leu-Gln-Asn (also referred to herein in the one-letter code as T-G-R-L-S-S-$X_{b7}$-$X_{b8}$-P-N-L-Q-N (SEQ ID NO:26));
wherein
$X_{b7}$ is Ser (S) or Thr (T);
$X_{b8}$ is Asp (D), Glu (E) or Asn (N).

In some embodiments, the mutant polymerase comprises the amino acid substitution at position $X_{13}$ in combination with the amino acid substitutions (other than those residues shown below for $X_{c4}$ and/or $X_{c6}$) at position $X_{c4}$ and/or $X_{c6}$ of DNA polymerases having a functional polymerase domain comprising the following amino acid motif:

Xaa-Xaa-Xaa-Xaa-Xaa-Xaa-Xaa-Asp-Tyr-Ser-Gln-Ile-Glu-Leu-Arg (also referred to herein in the one-letter code as $X_{c1}$-$X_{c2}$-$X_{c3}$-$X_{c4}$-$X_{c5}$-$X_{c6}$-$X_{c7}$-D-Y-S-Q-I-E-L-R (SEQ ID NO:27); wherein
$X_{c1}$ is Gly (G), Asn (N), or Asp (D);
$X_{c2}$ is Trp (W) or His (H);
$X_{c3}$ is Trp (W), Ala (A), Leu (L) or Val (V);
$X_{c4}$ is Ile (I) or Leu (L);
$X_{c5}$ is Val (V), Phe (F) or Leu (L);
$X_{c6}$ is Ser (S), Ala (A), Val (V) or Gly (G); and
$X_{c7}$ is Ala (A) or Leu (L).

In certain variations of the invention, the mutant polymerase comprises an amino acid substitution at position $X_{13}$, relative to a CS5 DNA polymerase or a CS6 DNA polymerase that is otherwise identical. Exemplary CS5 DNA polymerase and CS6 DNA polymerase mutants include those comprising the amino acid substitution E558G. Other, exemplary CS5 DNA polymerase and CS6 DNA polymerase mutants include the following (each having the amino acid sequence of SEQ ID NO:20 or SEQ ID NO:21 except for the designated substitutions):

E558G Q601R;
E558G D640G;
E558G I669F;
E558G S671F;
E558G D640G S671F;
E558G Q601R S671F;
E558G I669F S671F;
E558G Q601R D640G;
E558G D640G I669F;
E558G Q601R I669F;
E558G S671F D640G Q601R;
E558G S671F D640G I669F;
E558G S671F Q601R I669F;
E558G D640G Q601R I669F; and
E558G Q601R D640G I669F S671F;
wherein the Q601R amino acid substitution corresponds to an amino acid substitution at position $X_{a8}$; the D640G amino acid substitution corresponds to an amino acid substitution at position $X_{b8}$; the I669F amino acid substitution corresponds to an amino acid substitution at position $X_{c4}$; the S671F amino acid substitution corresponds to an amino acid substitution at position $X_{c6}$.

In some embodiments, the unmodified form of the chimeric polymerase includes one or more amino acid substitutions relative to SEQ ID NO:20 or SEQ ID NO:21 that are selected from G46E, L329A, and E678G, and further includes one or more amino acid substitutions relative to SEQ ID NO:20 or SEQ ID NO:21 that are selected from S671F, D640G, Q601R, and I669F. For example, the unmodified form of the mutant polymerase can be G46E L329A S671F E678G CS5; or the like. In exemplary embodiments, these unmodified forms are substituted to provide a mutant polymerase with a E558G substitutions. For example, the mutant DNA polymerase can be E558G G46E L329A S671F E678G CS5 or the like.

Accordingly, the mutation of the motif of SEQ ID NO:1, alone or in combination with other amino acid substitutions at other positions, confers an improved nucleic acid extension rate relative to an otherwise identical DNA polymerase. Various tests well-known to person skilled in the art can be used to measure the nucleic acid extension rate. In some embodiments, such tests are performed to compare a DNA polymerase comprising the motif of SEQ ID NO:1 with another DNA polymerase that has the same amino acid sequence at every position except for a single substitution at position $X_{13}$. In some embodiments, such tests are performed to compare a DNA polymerase comprising the motif of SEQ ID NO:1 with another DNA polymerase that has the same amino acid sequence at every position except for a substitution at position $X_{13}$ and substitutions at other positions, as described herein.

In addition to mutation of the motif of SEQ ID NO:1 as described herein, the mutant DNA polymerases of the present invention can also include other, non-substitutional modification(s). Such modifications can include, for example, covalent modifications known in the art to confer an additional advantage in applications comprising primer extension. For example, in certain embodiments, the mutant DNA polymerase further includes a thermally reversible covalent modification. In these embodiments, a modifier group is covalently attached to the protein, resulting in a loss of all, or nearly all, of the enzyme activity. The modifier group is chosen so that the modification is reversed by incubation at an elevated temperature. DNA polymerases comprising such thermally reversible modifications are particularly suitable for hot-start applications, such as, e.g., various hot-start PCR techniques. Thermally reversible modifier reagents amenable to use in accordance with the mutant DNA polymerases of the present invention are described in, for example, U.S. Pat. No. 5,773,258 to Birch et al., which is incorporated by reference herein. Exemplary modifications include, e.g., reversible blocking of lysine residues by chemical modification of the ε-amino group of lysine residues (see Birch et al., supra). In certain variations, the thermally reversible covalent modification includes covalent attachment, to the ε-amino group of lysine residues, of a dicarboxylic anhydride as described in Birch et al., supra.

For example, particularly suitable mutant polymerases comprising a thermally reversible covalent modification are produced by a reaction, carried out at alkaline pH at a temperature which is less than about 25° C., of a mixture of a thermostable enzyme and a dicarboxylic acid anhydride having a general formula as set forth in the following formula I:

where $R_1$ and $R_2$ are hydrogen or organic radicals, which may be linked; or having the following formula II:

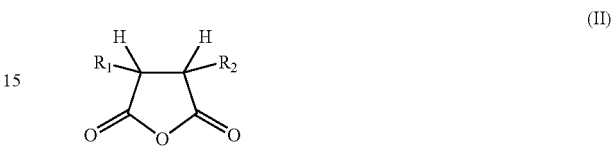

where $R_1$ and $R_2$ are organic radicals, which may linked, and the hydrogens are cis, essentially as described in Birch et al, supra. In specific embodiments comprising a thermally reversible covalent modification, the unmodified form of the polymerase is G64E CS5 DNA polymerase.

The mutant DNA polymerases of the present invention can be constructed by mutating the DNA sequences that encode the corresponding unmodified polymerase (e.g., a wild-type polymerase or a corresponding variant from which the mutant polymerase of the invention is derived), such as by using techniques commonly referred to as site-directed mutagenesis. Nucleic acid molecules encoding the unmodified form of the polymerase can be mutated by a variety of polymerase chain reaction (PCR) techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

By way of non-limiting example, the two primer system, utilized in the Transformer Site-Directed Mutagenesis kit from Clontech, may be employed for introducing site-directed mutants into a polynucleotide encoding an unmodified form of the polymerase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by, for example, microbore HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

DNA polymerases of the invention with more than one amino acid substituted can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified polymerase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (*Anal. Biochem.* 324:285-291. 2004) may be utilized.

Accordingly, also provided are recombinant nucleic acids encoding any of the DNA polymerases of the present invention. Using a nucleic acid of the present invention, encoding a DNA polymerase of the invention, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant DNA polymerase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the polymerase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the mutant polymerase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)).

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a mutant DNA polymerase is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, LIPOFECTIN®, electroporation, viral infection, and the like.

Prokaryotes are typically used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include E. coli K12 strain 94 (ATCC No. 31,446), E. coli strain W3110 (ATCC No. 27,325), E. coli K12 strain DG116 (ATCC No. 53,606), E. coli X1776 (ATCC No. 31,537), and E. coli B; however many other strains of E. coli, such as HB101, JM101, NM522, NM538, NM539, and many other species and genera of prokaryotes including bacilli such as Bacillus subtilis, other enterobacteriaceae such as Salmonella typhimurium or Serratia marcesans, and various Pseudomonas species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.*, 204:63, 1991. Plasmids typically used for transformation of E. coli include pBR322, pUCI8, pUCI9, pUCI18, pUC119, and Bluescript M13, all of which are described in sections 1.12-1.20 of Sambrook et al., supra. However, many other suitable vectors are available as well.

The DNA polymerases of the present invention are typically produced by culturing a host cell transformed with an expression vector containing a nucleic acid encoding the mutant DNA polymerase, under the appropriate conditions to induce or cause expression of the mutant DNA polymerase. Methods of culturing transformed host cells under conditions suitable for protein expression are well-known in the art (see, e.g., Sambrook et al., supra). Suitable host cells for production of the mutant polymerases from lambda pL promotor-containing plasmid vectors include E. coli strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the mutant polymerase can be harvested and isolated. Methods for purifying the thermostable DNA polymerase are described in, for example, Lawyer et al., supra.

Once purified, the ability of the mutant DNA polymerases to extend primed templates can be tested in any of various known assays for measuring extension. For example, in the presence of primed template molecules (e.g., M13 DNA, etc.), an appropriate buffer, a complete set of dNTPs (e.g., dATP, dCTP, dGTP, and dTTP), and metal ion, DNA polymerases will extend the primers, converting single-stranded DNA (ssDNA) to double-stranded DNA (dsDNA). This conversion can be detected and quantified by, e.g., adding a dsDNA-binding dye, such as SYBR Green I. Using a kinetic thermocycler (see, Watson, et al. *Anal. Biochem.* 329:58-67, 2004, and also available from, e.g., Applied Biosystems, Stratagene, and BioRad), digital images of reaction plates can be taken (e.g., at 10-30 second intervals), thereby allowing the progress of the reactions to be followed. The amount of fluorescence detected can be readily converted to extension rates. Using such routine assays, extension rates of the mutants relative to the unmodified forms of polymerase can be determined.

The DNA polymerases of the present invention may be used for any purpose in which such enzyme activity is necessary or desired. Accordingly, in another aspect of the invention, methods of primer extension using the DNA polymerases of the invention are provided. Conditions suitable for primer extension are known in the art. (See, e.g., Sambrook et al., supra. See also Ausubel et al., *Short Protocols in Molecular Biology* (4th ed., John Wiley & Sons 1999). Generally, a primer is annealed, i.e., hybridized, to a target nucleic acid to form a primer-template complex. The primer-template complex is contacted with the mutant DNA polymerase and free nucleotides in a suitable environment to permit the addition of one or more nucleotides to the 3' end of the primer, thereby producing an extended primer complementary to the target nucleic acid. The primer can include, e.g., one or more nucleotide analog(s). In addition, the free nucleotides can be conventional nucleotides, unconventional nucleotides (e.g., ribonucleotides or labeled nucleotides), or a mixture thereof. In some variations, the primer extension reaction comprises amplification of a target nucleic acid. Conditions suitable for nucleic acid amplification using a DNA polymerase and a primer pair are also known in the art (e.g., PCR amplification methods). (See, e.g., Sambrook et al., supra; Ausubel et al., supra; *PCR Applications: Protocols for Functional Genomics* (Innis et al. eds., Academic Press 1999). In other, non-mutually exclusive embodiments, the primer extension reaction comprises reverse transcription of an RNA template (e.g., RT-PCR). Use of the present mutant polymerases, which provide an improved extension rate, allow for, e.g., the ability to perform such primer extension reactions with relatively short incubation times, decreased enzyme concentrations, and/or increased product yield.

In yet other embodiments, the DNA polymerases of the invention are used for primer extension in the context of DNA sequencing, DNA labeling, or labeling of primer extension products. For example, DNA sequencing by the Sanger dideoxynucleotide method (Sanger et al., *Proc. Natl. Acad. Sci. USA* 74: 5463, 1977) is improved by the present invention for polymerases capable of incorporating unconventional, chain-terminating nucleotides. Advances in the basic Sanger et al. method have provided novel vectors (Yanisch-Perron et al., *Gene* 33:103-119, 1985) and base analogues (Mills et al., *Proc. Natl. Acad. Sci. USA* 76:2232-2235, 1979; and Barr et al., *Biotechniques* 4:428-432, 1986). In general, DNA sequencing requires template-dependent primer extension in the presence of chain-terminating base analogs, resulting in a distribution of partial fragments that are subsequently separated by size. The basic dideoxy sequencing procedure involves (i) annealing an oligonucleotide primer, optionally labeled, to a template; (ii) extending the primer with DNA polymerase in four separate reactions, each containing a mixture of unlabeled dNTPs and a limiting amount of one chain terminating agent such as a ddNTP, optionally labeled; and (iii) resolving the four sets of reaction products on a high-resolution denaturing polyacrylamide/urea gel. The reaction products can be detected in the gel by autoradiography or by fluorescence detection, depending on the label used, and the image can be examined to infer the nucleotide sequence. These methods utilize DNA polymerase such as the Klenow fragment of E. coli Pol I or a modified T7 DNA polymerase.

The availability of thermostable polymerases, such as Taq DNA polymerase, resulted in improved methods for sequencing with thermostable DNA polymerase (see Innis et al., *Proc. Natl. Acad. Sci. USA* 85:9436, 1988) and modifications thereof referred to as "cycle sequencing" (Murray, *Nuc Acids Res.* 17:8889, 1989). Accordingly, mutant thermostable polymerases of the present invention can be used in conjunction with such methods. As an alternative to basic dideoxy sequencing, cycle sequencing is a linear, asymmetric amplification of target sequences complementary to the template sequence in the presence of chain terminators. A single cycle produces a family of extension products of all possible lengths. Following denaturation of the extension reaction product from the DNA template, multiple cycles of primer annealing and primer extension occur in the presence of terminators such as ddNTPs. Cycle sequencing requires less template DNA than conventional chain-termination sequencing. Thermostable DNA polymerases have several advantages in cycle sequencing; they tolerate the stringent annealing temperatures which are required for specific hybridization of primer to nucleic acid targets as well as tolerating the multiple cycles of high temperature denaturation which occur in each cycle, e.g., 90-95° C. For this reason, AMPLITAQ® DNA Polymerase and its derivatives and descendants, e.g., AmpliTaq CS DNA Polymerase and AmpliTaq FS DNA Polymerase have been included in Taq cycle sequencing kits commercialized by companies such as Perkin-Elmer (Norwalk, Conn.) and Applied Biosystems (Foster City, Calif.).

Variations of chain termination sequencing methods include dye-primer sequencing and dye-terminator sequencing. In dye-primer sequencing, the ddNTP terminators are unlabeled, and a labeled primer is utilized to detect extension products (Smith et al., *Nature* 32:674-679, 1986). In dye-terminator DNA sequencing, a DNA polymerase is used to incorporate dNTPs and fluorescently labeled ddNTPs onto the end of a DNA primer (Lee et al., *Nuc. Acids. Res.* 20:2471, 1992). This process offers the advantage of not having to synthesize dye labeled primers. Furthermore, dye-terminator reactions are more convenient in that all four reactions can be performed in the same tube.

Both dye-primer and dye-terminator methods may be automated using an automated sequencing instrument produced by Applied Biosystems (Foster City, Calif.) (U.S. Pat. No. 5,171,534, which is herein incorporated by reference). When using the instrument, the completed sequencing reaction mixture is fractionated on a denaturing polyacrylamide gel or capillaries mounted in the instrument. A laser at the bottom of the instrument detects the fluorescent products as they are electrophoresed according to size through the gel.

Two types of fluorescent dyes are commonly used to label the terminators used for dye-terminator sequencing-negatively charged and zwitterionic fluorescent dyes. Negatively charged fluorescent dyes include those of the fluorescein and BODIPY families. BODIPY dyes (4,4-difluoro-4-bora-3a, 4a-diaza-s-indacene) are described in International Patent Publication WO 97/00967, which is incorporated herein by reference. Zwitterionic fluorescent dyes include those of the rhodamine family. Commercially available cycle sequencing kits use terminators labeled with rhodamine derivatives. However, the rhodamine-labeled terminators are rather costly and the product must be separated from unincorporated dye-ddNTPs before loading on the gel since they co-migrate with the sequencing products. Rhodamine dye family terminators seem to stabilize hairpin structures in GC-rich regions, which causes the products to migrate anomalously. This requires the use of dITP, which relaxes the secondary structure but also affects the efficiency of incorporation of terminator.

In contrast, fluorescein-labeled terminators eliminate the separation step prior to gel loading since they have a greater net negative charge and migrate faster than the sequencing products. In addition, fluorescein-labeled sequencing products have better electrophoretic migration than sequencing products labeled with rhodamine. Although wild-type Taq DNA polymerase does not efficiently incorporate terminators labeled with fluorescein family dyes, this can now be accomplished efficiently by use of the modified enzymes as described in U.S. Patent Application Publication No. 2002/0142333, which is incorporated by reference herein in its entirety. Accordingly, modifications as described in US 2002/0142333 can be used in the context of the present invention to produce fluorescein-family-dye-incorporating thermostable polymerases having improved primer extension rates. For example, in certain embodiments, the unmodified DNA polymerase in accordance with the present invention is a modified thermostable polymerase as described in US 2002/0142333 and having the motif set forth in SEQ ID NO:1.

Other exemplary nucleic acid sequencing formats in which the DNA polymerases of the invention can be used include those involving terminator compounds that include 2'-$PO_4$ analogs of ribonucleotides (see, e.g., U.S. Application Publication Nos. 2005/0037991 and 2005/0037398, and U.S. patent application Ser. No. 11/583,605, entitled "SYNTHESIS AND COMPOSITIONS OF NUCLEIC ACIDS COMPRISING 2'-TERMINATOR NUCLEOSIDES", filed Oct. 19, 2006 by Bodepudi et al. and U.S. patent application Ser. No. 11/583,606, entitled "2'-TERMINATOR RELATED PYROPHOSPHOROLYSIS ACTIVATED POLYMERIZATION", filed Oct. 19, 2006 by Gelfand et al., which are each incorporated by reference). The DNA polymerases described herein generally improve these sequencing methods, e.g., by reducing the time necessary for the cycled extension reactions and/or by reducing the amount or concentration of enzyme that is utilized for satisfactory performance.

In another aspect of the present invention, kits are provided for use in primer extension methods described herein. Typically, the kit is compartmentalized for ease of use and contains at least one container providing a mutant DNA polymerase in accordance with the present invention. One or more additional containers providing additional reagent(s) can also be included. Such additional containers can include any reagents or other elements recognized by the skilled artisan for use in primer extension procedures in accordance with the methods described above, including reagents for use in, e.g., nucleic acid amplification procedures (e.g., PCR, RT-PCR), DNA sequencing procedures, or DNA labeling procedures. For example, in certain embodiments, the kit further includes a container providing a 5' sense primer hybridizable, under primer extension conditions, to a predetermined polynucleotide template, or a primer pair comprising the 5' sense primer and a corresponding 3' antisense primer. In other, non-mutually exclusive variations, the kit includes one or more containers providing free nucleotides (conventional and/or unconventional). In specific embodiments, the kit includes alpha-phosphorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example I

Identification and Characterization of a Mutant DNA Polymerase with Improved Extension Activity A mutation in CS family polymerases were identified that provide, e.g., improved ability to extend primed DNA templates in the presence of free nucleotides. In brief, the steps in this screening process included library generation, expression and partial purification of mutant enzymes, screening of the enzymes for the desired property, DNA sequencing, clonal purification, and further characterization of selected mutants. Each of these steps is described further below.

The mutation identified by this process was E558G. The mutation resulted in an improved ability to extend primed templates. In the particular context of the E678G mutation, which allows for the incorporation of ribonucleotides and other 2'-modified nucleotides, but which also results in an impaired ability to extend primed templates, the E558G mutation ameliorated this property of impaired primer extension ability.

Clonal Library generation: A nucleic acid encoding the polymerase domain of CS5 E678G DNA polymerase was subjected to error-prone mutagenic PCR. PCR was performed using a range of $Mg^{+2}$ concentrations from 1.8-3.5 mM, in order to generate libraries with a corresponding range of mutation rates. Buffer conditions were: 50 mM Bicine pH 8.2, 115 mM KOAc, 8% w/v glycerol, 0.2 mM each dNTPs, and 0.2×SYBR Green I. A GeneAmp® AccuRT Hot Start PCR enzyme was used at 0.15 U/µl. Starting with $5\times10^5$ copies of linearized CS5 E678G plasmid DNA/reaction volume of 50 µl, 30 cycles of amplification were performed, using an annealing temperature of 60° C. for 15 seconds, an extension temperature of 72° C. for 45 seconds, and a denaturation temperature of 95° C. for 15 seconds.

The resulting amplicon was purified over a Qiaquick spin column (Qiagen, Inc., Valencia, Calif., USA) and cut with Bgl II and Hind III, then re-purified. A vector plasmid, a modification of G46E L329A CS5 carrying a large deletion in the polymerase domain between the BglII and HindIII sites, was prepared by cutting with the same two restriction enzymes and treating with calf intestinal phosphatase (CIP). The cut vector and the mutated insert were mixed at different ratios and treated with T4 ligase overnight at 15° C. The ligations were purified and transformed into E. coli strain LK3 by electroporation.

Aliquots were plated on ampicillin-selective medium in order to determine the number of unique transformants in each transformation. Transformations with the most unique transformants at each mutagenesis rate were stored at −70 to −80° C. in the presence of glycerol as a cryo-protectant.

Each library was then spread on large format ampicillin-selective agar plates. Individual colonies were transferred to 384-well plates containing 2× Luria broth with ampicillin and 10% w/v glycerol using an automated colony picker (QPix2, Genetix Ltd). These plates were incubated overnight at 30° C. to allow the cultures to grow, then stored at −70 to −80° C. The glycerol added to the 2× Luria broth was low enough to permit culture growth and yet high enough to provide cryo-protection. Several thousand colonies at several mutagenesis ($Mg^+_2$) levels were prepared in this way for later use.

Extract library preparation Part 1—Fermentation: From the clonal libraries described above, a corresponding library of partially purified extracts suitable for screening purposes was prepared. The first step of this process was to make small-scale expression cultures of each clone. These cultures were grown in 96-well format; therefore there were 4 expression culture plates for each 384-well library plate. One µl was transferred from each well of the clonal library plate to a well of a 96 well seed plate, containing 150 µl of Medium A (see Table 3 below). This seed plate was shaken overnight at 1150 rpm at 30° C., in an iEMS plate incubater/shaker (Thermo-Electron). These seed cultures were then used to inoculate the same medium, this time inoculating 10 µl into 300 µl Medium A in large format 96 well plates (Nunc # 267334). These plates were incubated overnight at 37° C. The expression plasmid contained transcriptional control elements which allow for expression at 37° C. but not at 30° C. After overnight incubation, the cultures expressed the clone protein at typically 1-10% of total cell protein. The cells from these cultures were harvested by centrifugation. These cells were either frozen (−20° C.) or processed immediately, as described below.

TABLE 3

| Medium A (Filter-sterilized prior to use) | |
|---|---|
| Component | Concentration |
| $MgSO_4 \cdot 7H_2O$ | 0.2 g/L |
| Citric acid•$H_2O$ | 2 g/L |
| $K_2HPO_4$ | 10 g/L |
| $NaNH_4PO_4 \cdot 4H_2O$ | 3.5 g/L |
| $MgSO_4$ | 2 mM |
| Casamino acids | 2.5 g/L |
| Glucose | 2 g/L |
| Thiamine•HCl | 10 mg/L |
| Ampicillin | 100 mg/L |

Extract library preparation Part 2—Extraction: Cell pellets from the fermentation step were resuspended in 30 µl Lysis buffer (Table 4 below) and transferred to 384-well thermocycler plates. Note that the buffer contains lysozyme to assist in cell lysis, and two nucleases to remove both RNA and DNA from the extract. The plates were subjected to three rounds of freeze-thaw (−70° C. freeze, 37° C. thaw, not less than 15 minutes per step) to lyse the cells. Ammonium sulfate was added (5 µl of a 0.75M solution) and the plates incubated at 75° C. for 15 minutes in order to precipitate and inactivate contaminating proteins, including the exogenously added nucleases. The plates were centrifuged at 3000×g for 15 minutes and the supernatants transferred to a fresh 384 well thermocycler plate. These extract plates were frozen at −20° C. for later use in screens. Each well contained about 0.5-3 µM of the mutant polymerase enzyme.

TABLE 4

| Lysis Buffer | |
|---|---|
| Component | Concentration or Percentage |
| Tris pH 8.0 | 20 mM |
| EDTA | 1 mM |
| $MgCl_2$ | 5 mM |
| TLCK | 1 mM |
| Leupeptin | 1 µg/ml |
| Pefabloc | 0.5 mg/ml |
| Tween 20 | 0.5% v/v |
| Lysozyme (from powder) | 2 mg/ml |
| Rnase | 0.025 mg/ml |
| Dnase I | 0.075 Units/µl |

Screening Extract Libraries for improved extension rate: M13mp18 single-stranded DNA (M13 DNA), primed with an oligonucleotide having the following sequence:

(SEQ ID NO: 28)
5'-GGGAAGGGCGATCGGTGCGGGCCTCTTCGC-3' was used as the template molecule in the extension assay screen. In this screen, extracts plates described above were diluted 10-fold in 10 mM Tris pH 8.0/1 mM EDTA/100 mM KCl/0.2% Tween 20, and heat-treated at 90° C. for 10 minutes, to increase their purity. 1.0 µl extract was added to 13 µl reaction master mix containing 1 nM primed M13 template in 384 well PCR plates. Extension of the primed template at 64° C. was monitored every 20 seconds in a modified kinetic thermal cycler using a CCD camera. A typical reaction master mix is listed below. The reaction mix also contained 100 mM Tricine pH 8.0, 20 mM KOAc, 3 mM MgCl2, 2.5% v/v Enzyme Storage Buffer containing 0.5% Tween 20, 0.1 mM each dATP, dCTP, dGTP, and dTTP, and SYBR Green I at 0.6× (Molecular Probes), which allowed for the fluorescent detection of primer strand extension. In order to distinguish extension-derived fluorescence from background fluorescence, parallel wells were included in the experiment in which primer strand extension was prevented, for example, by adding a metal chelator such as EDTA, or leaving out the nucleotides from the reaction master mix.

Mutant extracts which exhibited increased rate of extension were identified in this screen. Primary screening was done on the scale of thousands of extracts. Culture wells corresponding to the top extracts were chosen for further testing. They were first streaked on selective agar plates to ensure clonal purity. Mutant enzyme was purified from 100 ml shake flask cultures and the concentration determined by gel-based densitometry. These quantified enzyme preps were compared to parental enzyme in the conditions used in the screen, but at equal protein concentration. This final screen ensured that the differences observed were not simply protein concentration effects.

Following this final round of screening, five clones still appeared to have improved extension rates. The sequences of these clones were determined to code for the following amino acid changes relative to the parental strain:
  clone 1: S671F
  clone 2: S671F
  clone 3: Q610R E779K I812L M8441
  clone 4: E558G I829V
  clone 5: E558G K861M
In the case of clones 1 and 2, it is clear that the S671F mutation must have been responsible for the observed phenotype, since it was the only amino acid mutation in the clone.

For clone 3, the phenotype is most probably the result of the Q601R mutation, based on other results. Since both clones 4 and 5 carry the same E558G mutation, it seemed that this mutation was most probably responsible for the observed phenotype. To confirm this, a parental clone (G46E L329A E678G CS5 DNA polymerase; "GLE") was mutated to carry an additional E558G mutation (G46E L329A E558G E678G CS5 DNA Polymerase; "GLEE") using the well known technique of in vitro mutagenesis by overlap PCR. The resulting plasmid was sequenced to confirm that it carried the desired mutation and no other unintended mutations which are occasionally generated during the PCR steps of this process The new plasmid were transformed into the E. coli strain LK3 host, and polymerase protein was expressed, purified to homogeneity, and quantified. These resulting new mutant enzymes were compared to the parental types and to other mutants, under conditions similar to the original screen. The results are shown in FIG. 4. The strain carrying the E558G mutation, "GLEE", was over 12 times faster at extending primed M13 than the parental clone "GLE" under the conditions of this test. It was clear from this data that the mutation E558G was solely responsible for the improved phenotype of mutant clones 4 and 5. The Figure also shows the relative rate of certain other mutations in the GLE backbone, such as D640G ("GLDE"), D573G ("997-01"), Q601R ("GLQE"), S671F ("GLSE"), as well as clones carrying multiple mutations, such as the combination of Q601R, S671F, and D640G ("GLQDSE"), and finally E558G in combination with Q601R, S671F, and D640G ("GLEQDSE").

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A DNA polymerase wherein the polymerase has at least 90% sequence identity to SEQ ID NO:20 or SEQ ID NO:21, comprising A-G-$X_1$-$X_2$-F-$X_3$-$X_4$-$X_5$-S-$X_6$-$X_7$-Q-$X_8$-$X_9$-$X_{10}$-$X_{11}$-L-$X_{12}$-$X_{13}$-$X_{14}$-$X_{15}$(SEQ ID NO:33), wherein $X_2$, $X_5$, $X_6$, $X_9$, and $X_{10}$ are any amino acid,
$X_1$ is H, E or Q,
$X_3$ is N or H,
$X_4$ is L or I,
$X_7$ is D, K or T,
$X_8$ is L or V,
$X_{11}$ is V, I or L,
$X_{12}$ is F or Y,
$X_{13}$ is G,
$X_{14}$ is K or E, and
$X_{15}$ is L or Q;
wherein the polymerase has an increased nucleic acid extension rate relative to a DNA polymerase that is identical with the exception that $X_{13}$ is E.

2. The DNA polymerase of claim 1, wherein
$X_2$ is selected from the group consisting of P, A, E, T, and V;
$X_5$ is selected from the group consisting of N, R, G, and S;
$X_6$ is selected from the group consisting of R, P, S, and T;
$X_9$ is selected from the group consisting of E, G, Q, S, and A; and
$X_{10}$ is selected from the group consisting of R, T, A, V, Y, S, and N.

3. The DNA polymerase of claim 1, wherein the polymerase comprises a chimeric polymerase.

4. The DNA polymerase of claim 3, wherein the chimeric polymerase comprises SEQ ID NO:20 or SEQ ID NO:21 or one or more amino acid substitutions relative to SEQ ID NO:20 or SEQ ID NO:21 that are selected from the group consisting of: G46E, L329A, and E678G.

5. The DNA polymerase of claim 1, further comprising a thermally reversible covalent modification.

6. The DNA polymerase of claim 5, wherein the polymerase comprising the thermally reversible covalent modification is produced by a reaction, carried out at alkaline pH at a temperature which is less than about 25° C., of a mixture of a thermostable DNA polymerase and a dicarboxylic acid anhydride having a general formula selected from the group consisting of (a) formula I:

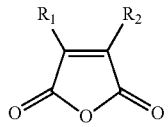

(I)

wherein $R_1$ and $R_2$ are hydrogen or organic radicals, which may be linked; and (b) formula II:

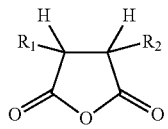

(II)

wherein $R_1$ and $R_2$ are organic radicals, which may linked, and the hydrogens are cis.

7. A method for conducting primer extension, comprising: contacting a DNA polymerase according to claim 1 with a primer, a polynucleotide template, and free nucleotides under conditions suitable for extension of the primer, thereby producing an extended primer.

8. The method of claim 7, wherein the polynucleotide template is an RNA.

9. The method of claim 7, wherein the polynucleotide template is a DNA.

10. The method according to claim 7, wherein the free nucleotides comprise unconventional nucleotides.

11. The method according to claim 10, wherein the unconventional nucleotides comprise ribonucleotides.

12. The method according to claim 10, wherein the unconventional nucleotides comprise labeled nucleotides.

13. The method of claim 7, wherein the primer comprises one or more nucleotide analog(s).

14. The method of claim 7, comprising contacting the DNA polymerase with a primer pair, the polynucleotide template, and the free nucleotides under conditions suitable for amplification of the polynucleotide.

15. A kit for producing an extended primer, comprising:
at least one container providing a DNA polymerase according to claim 1.

16. The kit according to claim 15, further comprising one or more additional containers selected from the group consisting of:
(a) a container providing a primer hybridizable, under primer extension conditions, to a predetermined polynucleotide template;
(b) a container providing free nucleotides; and
(c) a container providing a buffer suitable for primer extension.

* * * * *

SEQUENCE LISTING

<160> NUMBER OF SEQ ID NOS: 33

<210> SEQ ID NO 1
<211> LENGTH: 21
<212> TYPE: PRT
<213> ORGANISM: Artificial Sequence
<220> FEATURE:
<223> OTHER INFORMATION: region from polymerase domain of modified
      improved thermostable DNA polymerase, polymerase domain motif
<221> NAME/KEY: MOD_RES
<222> LOCATION: (3)...(3)
<223> OTHER INFORMATION: Xaa = His, Glu or Gln
<221> NAME/KEY: MOD_RES
<222> LOCATION: (4)...(4)
<223> OTHER INFORMATION: Xaa = any amino acid
<221> NAME/KEY: MOD_RES
<222> LOCATION: (6)...(6)
<223> OTHER INFORMATION: Xaa = Asn or His
<221> NAME/KEY: MOD_RES
<222> LOCATION: (7)...(7)
<223> OTHER INFORMATION: Xaa = Leu or Ile
<221> NAME/KEY: MOD_RES
<222> LOCATION: (8)...(8)
<223> OTHER INFORMATION: Xaa = any amino acid
<221> NAME/KEY: MOD_RES
<222> LOCATION: (10)...(10)
<223> OTHER INFORMATION: Xaa = any amino acid

```
<221> NAME/KEY: MOD_RES
<222> LOCATION: (11)...(11)
<223> OTHER INFORMATION: Xaa = Asp, Lys or Thr
<221> NAME/KEY: MOD_RES
<222> LOCATION: (13)...(13)
<223> OTHER INFORMATION: Xaa = Leu or Val
<221> NAME/KEY: MOD_RES
<222> LOCATION: (14)...(15)
<223> OTHER INFORMATION: Xaa = any amino acid
<221> NAME/KEY: MOD_RES
<222> LOCATION: (16)...(16)
<223> OTHER INFORMATION: Xaa = Val, Ile or Leu
<221> NAME/KEY: MOD_RES
<222> LOCATION: (18)...(18)
<223> OTHER INFORMATION: Xaa = Phe or Tyr
<221> NAME/KEY: MOD_RES
<222> LOCATION: (19)...(19)
<223> OTHER INFORMATION: Xaa = Ala, Cys, Phe, Gly, His, Ile, Lys, Met,
      Asn, Pro, Gln, Arg, Ser, Thr, Val, Trp or Tyr, an amino acid other
      than Asp or Glu
<221> NAME/KEY: MOD_RES
<222> LOCATION: (20)...(20)
<223> OTHER INFORMATION: Xaa = Lys or Glu
<221> NAME/KEY: MOD_RES
<222> LOCATION: (21)...(21)
<223> OTHER INFORMATION: Xaa = Leu or Gln

<400> SEQUENCE: 1

Ala Gly Xaa Xaa Phe Xaa Xaa Xaa Ser Xaa Xaa Gln Xaa Xaa Xaa Xaa
 1               5                  10                  15

Leu Xaa Xaa Xaa Xaa
            20

<210> SEQ ID NO 2
<211> LENGTH: 21
<212> TYPE: PRT
<213> ORGANISM: Artificial Sequence
<220> FEATURE:
<223> OTHER INFORMATION: region from polymerase domain of modified
      improved thermostable DNA polymerase, polymerase domain motif
<221> NAME/KEY: MOD_RES
<222> LOCATION: (1)...(1)
<223> OTHER INFORMATION: Xaa = Ala or Val
<221> NAME/KEY: MOD_RES
<222> LOCATION: (2)...(2)
<223> OTHER INFORMATION: Xaa = Gly or Val
<221> NAME/KEY: MOD_RES
<222> LOCATION: (3)...(3)
<223> OTHER INFORMATION: Xaa = His, Glu or Gln
<221> NAME/KEY: MOD_RES
<222> LOCATION: (4)...(4)
<223> OTHER INFORMATION: Xaa = any amino acid
<221> NAME/KEY: MOD_RES
<222> LOCATION: (6)...(6)
<223> OTHER INFORMATION: Xaa = Asn or His
<221> NAME/KEY: MOD_RES
<222> LOCATION: (7)...(7)
<223> OTHER INFORMATION: Xaa = Leu, Ile or Pro
<221> NAME/KEY: MOD_RES
<222> LOCATION: (8)...(8)
<223> OTHER INFORMATION: Xaa = any amino acid
<221> NAME/KEY: MOD_RES
<222> LOCATION: (10)...(10)
<223> OTHER INFORMATION: Xaa = any amino acid
<221> NAME/KEY: MOD_RES
<222> LOCATION: (11)...(11)
<223> OTHER INFORMATION: Xaa = Asp, Lys or Thr
<221> NAME/KEY: MOD_RES
<222> LOCATION: (12)...(12)
<223> OTHER INFORMATION: Xaa = Gln or His
<221> NAME/KEY: MOD_RES
<222> LOCATION: (13)...(13)
<223> OTHER INFORMATION: Xaa = Leu, Val or Ile
<221> NAME/KEY: MOD_RES
<222> LOCATION: (14)...(15)
<223> OTHER INFORMATION: Xaa = any amino acid
<221> NAME/KEY: MOD_RES
```

```
<222> LOCATION: (16)...(16)
<223> OTHER INFORMATION: Xaa = Val, Ile, Leu or Lys
<221> NAME/KEY: MOD_RES
<222> LOCATION: (18)...(18)
<223> OTHER INFORMATION: Xaa = Phe, Tyr or Gln
<221> NAME/KEY: MOD_RES
<222> LOCATION: (19)...(19)
<223> OTHER INFORMATION: Xaa = Ala, Cys, Phe, Gly, His, Ile, Lys, Met,
      Asn, Pro, Gln, Arg, Ser, Thr, Val, Trp or Tyr, an amino acid other
      than Asp or Glu
<221> NAME/KEY: MOD_RES
<222> LOCATION: (20)...(20)
<223> OTHER INFORMATION: Xaa = Lys, Glu or Ala
<221> NAME/KEY: MOD_RES
<222> LOCATION: (21)...(21)
<223> OTHER INFORMATION: Leu, Gln or Gly

<400> SEQUENCE: 2

Xaa Xaa Xaa Xaa Phe Xaa Xaa Xaa Ser Xaa Xaa Xaa Xaa Xaa Xaa Xaa
 1               5                  10                  15

Leu Xaa Xaa Xaa Xaa
         20

<210> SEQ ID NO 3
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus thermophilus
      (Tth)

<400> SEQUENCE: 3

Phe Arg Leu Ala Gly His Pro Phe Asn Leu Asn Ser Arg Asp Gln Leu
 1               5                  10                  15

Glu Arg Val Leu Phe Asp Glu Leu Arg Leu
         20                  25

<210> SEQ ID NO 4
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus caldophilus (Tca)

<400> SEQUENCE: 4

Phe Arg Leu Ala Gly His Pro Phe Asn Leu Asn Ser Arg Asp Gln Leu
 1               5                  10                  15

Glu Arg Val Leu Phe Asp Glu Leu Arg Leu
         20                  25

<210> SEQ ID NO 5
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus sp. Z05 (Z05)

<400> SEQUENCE: 5

Phe Arg Leu Ala Gly His Pro Phe Asn Leu Asn Ser Arg Asp Gln Leu
 1               5                  10                  15

Glu Arg Val Leu Phe Asp Glu Leu Arg Leu
         20                  25

<210> SEQ ID NO 6
<211> LENGTH: 26
```

-continued

```
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus aquaticus (Taq)

<400> SEQUENCE: 6

Phe Arg Leu Ala Gly His Pro Phe Asn Leu Asn Ser Arg Asp Gln Leu
1               5                   10                  15

Glu Arg Val Leu Phe Asp Glu Leu Gly Leu
            20                  25

<210> SEQ ID NO 7
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus flavus (Tfl)

<400> SEQUENCE: 7

Phe Arg Leu Ala Gly His Pro Phe Asn Leu Asn Ser Arg Asp Gln Leu
1               5                   10                  15

Glu Arg Val Leu Phe Asp Glu Leu Gly Leu
            20                  25

<210> SEQ ID NO 8
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus filiformis (Tfi)

<400> SEQUENCE: 8

His Arg Leu Ala Gly His Pro Phe Asn Leu Asn Ser Arg Asp Gln Leu
1               5                   10                  15

Glu Arg Val Leu Phe Asp Glu Leu Gly Leu
            20                  25

<210> SEQ ID NO 9
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermus sp. sps17 (Sps17)

<400> SEQUENCE: 9

His Arg Leu Ala Gly His Pro Phe Asn Leu Asn Ser Arg Asp Gln Leu
1               5                   10                  15

Glu Arg Val Leu Phe Asp Glu Leu Gly Leu
            20                  25

<210> SEQ ID NO 10
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Deinococcus radiodurans
      (Dra)

<400> SEQUENCE: 10

His Glu Tyr Ala Gly Glu Glu Phe His Ile Arg Ser Pro Lys Gln Leu
1               5                   10                  15
```

-continued

Glu Thr Val Leu Tyr Asp Lys Leu Glu Leu
            20                  25

<210> SEQ ID NO 11
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Hot Spring family B/clone
      7 (HspB)

<400> SEQUENCE: 11

Tyr Thr Leu Ala Gly Glu Ala Phe Asn Ile Gly Ser Pro Lys Gln Leu
 1               5                  10                  15

Gly Ala Ile Leu Phe Glu Lys Leu Gly Leu
            20                  25

<210> SEQ ID NO 12
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Bacillus
      stearothermophilus (Bst)

<400> SEQUENCE: 12

Tyr Glu Leu Ala Gly Gln Glu Phe Asn Ile Asn Ser Pro Lys Gln Leu
 1               5                  10                  15

Gly Thr Val Leu Phe Asp Lys Leu Gln Leu
            20                  25

<210> SEQ ID NO 13
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Bacillus caldotenax (Bca)

<400> SEQUENCE: 13

Tyr Glu Leu Ala Gly Gln Glu Phe Asn Ile Asn Ser Pro Lys Gln Leu
 1               5                  10                  15

Gly Val Ile Leu Phe Glu Lys Leu Gln Leu
            20                  25

<210> SEQ ID NO 14
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Escherichia coli (Eco)

<400> SEQUENCE: 14

His Glu Ile Ala Gly Glu Glu Phe Asn Leu Ser Ser Thr Lys Gln Leu
 1               5                  10                  15

Gln Thr Ile Leu Phe Glu Lys Gln Gly Ile
            20                  25

<210> SEQ ID NO 15
<211> LENGTH: 26
<212> TYPE: PRT
<213> ORGANISM: Artificial Sequence
<220> FEATURE:
<223> OTHER INFORMATION: region from polymerase domain of thermostable DNA polymerase of thermophilic bacterium Thermotoga maritime (Tma)

<400> SEQUENCE: 15

Tyr Arg Ile Ala Gly Glu Pro Phe Asn Ile Asn Ser Pro Lys Gln Val
1               5                   10                  15

Ser Arg Ile Leu Phe Glu Lys Leu Gly Ile
            20                  25

<210> SEQ ID NO 16
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermotoga neapolitana
      (Tne)

<400> SEQUENCE: 16

Tyr Gln Ile Ala Gly Glu Pro Phe Asn Ile Asn Ser Pro Lys Gln Val
1               5                   10                  15

Ser Asn Ile Leu Phe Glu Lys Leu Gly Ile
            20                  25

<210> SEQ ID NO 17
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Thermosipho africanus
      (Taf)

<400> SEQUENCE: 17

Phe Glu Ile Ala Gly Glu Thr Phe Asn Leu Asn Ser Thr Gln Val
1               5                   10                  15

Ala Tyr Ile Leu Phe Glu Lys Leu Asn Ile
            20                  25

<210> SEQ ID NO 18
<211> LENGTH: 26
<212> TYPE: PRT
<213> ORGANISM: Artificial Sequence
<220> FEATURE:
<223> OTHER INFORMATION: region from polymerase domain of thermostable
      DNA polymerase of thermophilic bacterium Hot Spring family A
      (HspA)

<400> SEQUENCE: 18

Tyr Ala Gln Ala Gly Glu Val Phe Asn Leu Asn Ser Pro Lys Gln Leu
1               5                   10                  15

Gly Ser Leu Leu Phe Glu Lys Leu Lys Leu
            20                  25

<210> SEQ ID NO 19
<211> LENGTH: 24
<212> TYPE: PRT
<213> ORGANISM: Artificial Sequence
<220> FEATURE:
<223> OTHER INFORMATION: region from polymerase domain of thermostable
      DNA polymerase of Bacteriophage T7 (T7)

<400> SEQUENCE: 19

Val Glu His Val Val Phe Asn Pro Ser Ser Arg Asp His Ile Gln Lys
1               5                   10                  15

Lys Leu Gln Glu Ala Gly Trp Val
            20

<210> SEQ ID NO 20
<211> LENGTH: 893
<212> TYPE: PRT
<213> ORGANISM: Artificial Sequence
<220> FEATURE:
<223> OTHER INFORMATION: chimeric thermostable DNA polymerase CS5

<400> SEQUENCE: 20

Met Lys Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

-continued

```
Lys Leu Lys Glu Ile Leu Glu Asp Pro Gly Ala Lys Ile Val Gly Gln
        370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
                435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Tyr Gly Lys Lys
                515                 520                 525

Leu Glu Glu Leu Ala Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
    595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
                675                 680                 685

Glu Asn Leu Leu Arg Ala Phe Glu Glu Gly Ile Asp Val His Thr Leu
    690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
                755                 760                 765

Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800
```

```
Arg Asn Thr Gln Ala Glu Gly Glu Arg Ile Ala Ile Asn Thr Pro Ile
            805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
            850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890

<210> SEQ ID NO 21
<211> LENGTH: 893
<212> TYPE: PRT
<213> ORGANISM: Artificial Sequence
<220> FEATURE:
<223> OTHER INFORMATION: chimeric thermostable DNA polymerase CS6

<400> SEQUENCE: 21

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270
```

```
Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
290                 295                 300

Val Glu Phe Glu Lys Leu Ile Glu Lys Leu Arg Glu Ser Pro Ser Phe
305                 310                 315                 320

Ala Ile Ala Leu Ala Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
        530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly His Glu Ile Ile Pro
                580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
        610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
690                 695                 700
```

```
Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
            725                 730                 735

Thr Pro Tyr Gly Leu Ser Val Arg Leu Gly Val Pro Val Lys Glu Ala
        740                 745                 750

Glu Lys Met Ile Val Asn Tyr Phe Val Leu Tyr Pro Lys Val Arg Asp
    755                 760                 765

Tyr Ile Gln Arg Val Val Ser Glu Ala Lys Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 22
<211> LENGTH: 2682
<212> TYPE: DNA
<213> ORGANISM: Artificial Sequence
<220> FEATURE:
<223> OTHER INFORMATION: chimeric thermostable DNA polymerase CS5

<400> SEQUENCE: 22
atgaaagcta tgttaccatt attcgaaccc aaaggccggg tcctcctggt ggacggccac      60
cacctggcct accgcacctt cttcgccctg aagggcctca ccacgagccg ggcgaaccg     120 gtgcaggcgg tttacggctt cgccaagagc ctcctcaagg ccctgaagga ggacgggtac    180
aaggccgtct tcgtggtctt tgacgccaag gccccttcct tccgccacga ggcctacgag    240
gcctacaagg caggccgcgc cccgacccc gaggacttcc cccggcagct cgccctcatc     300
aaggagctgg tggacctcct ggggtttact cgcctcgagg ttccgggctt tgaggcggac    360
gacgtcctcg ccaccctggc caagaaggcg aaagggagg ggtacgaggt gcgcatcctc    420
accgccgacc gggaccttta ccagctcgtc tccgaccgcg tcgccgtcct ccaccccgag    480
ggccacctca tcaccccgga gtggcttttgg gagaagtacg gcttaagcc ggagcagtgg    540 gtggacttcc gcgccctcgt gggggacccc tccgacaacc tccccggggt caagggcatc    600
ggggagaaga ccgccctcaa gctcctcaag gagtggggaa gcctggaaaa tatcctcaag    660
aacctggacc gggtgaagcc ggaaagcgtc cgggaaagga tcaaggccca cctggaagac    720
cttaagctct ccttggagct ttcccgggtg cgctcggacc tcccctgga ggtggacttc    780 gcccggaggc gggagcctga ccgggaaggg cttcgggcct ttttgagcg cttggagttc    840 ggcagcctcc tccacgagtt cggccttcta gaggagtccg aacccgttgg gtaccgtata    900
gttaaagacc tggttgaatt tgaaaaactc atagagaaac tgagagaatc ccttcgttc    960 gctatcgatt tggaaactag ttccctcgat cctttcgact gcgacattgt cggtatctct   1020
```

-continued

```
gtgtctttca aaccaaagga agcgtactac ataccactcc atcatagaaa cgcccagaac      1080
ctggacgaaa aagaggttct gaaaaagctc aaagaaattc tggaggaccc cggagcaaag      1140
atcgttggtc agaatttgaa attcgattac aaggtgttga tggtgaaggg tgttgaacct      1200
gttcctcctt acttcgacac gatgatagcg gcttaccttc ttgagccgaa cgaaaagaag      1260
ttcaatctgg acgatctcgc attgaaattt cttggataca aaatgacatc ttaccaagag      1320
ctcatgtcct tctcttttcc gctgtttggt ttcagttttg ccgatgttcc tgtagaaaaa      1380
gcagcgaact actcctgtga agatgcagac atcacctaca gacttacaa gaccctgagc      1440
ttaaaactcc acgaggcaga tctggaaaac gtgttctaca gatagaaat gccccttgtg      1500
aacgtgcttg cacggatgga actgaacggt gtgtatgtgg acacagagtt cctgaagaaa      1560
ctctcagaag agtacggaaa aaaactcgaa gaactggcag aggaaatata caggatagct      1620
ggagagccgt tcaacataaa ctcaccgaag caggtttcaa ggatcctttt tgaaaaactc      1680
ggcataaaac cacgtggtaa aacgacgaaa acggagacta ttcaacacg catagaagtc      1740
ctcgaggaac ttgccggtga acacgaaatc attcctctga ttcttgaata cagaaagata      1800
cagaaattga aatcaaccta catagacgct cttcccaaga tggtcaaccc aaagaccgga      1860
aggattcatg cttctttcaa tcaaacgggg actgccactg gaagacttag cagcagcgat      1920
cccaatcttc agaacctccc gacgaaaagt gaagagggaa aagaaatcag gaaagcgata      1980
gttcctcagg atccaaactg gtggatcgtc agtgccgact actcccaaat gaactgagg       2040
atcctcgccc atctcagtgg tgatgagaat cttttgaggg cattcgaaga gggcatcgac      2100
gtccacactc taacagcttc cagaatattc aacgtgaaac ccgaagaagt aaccgaagaa      2160
atgcgccgcg ctggtaaaat ggttaatttt tccatcatat acggtgtaac accttacggt      2220
ctgtctgtga ggcttggagt acctgtgaaa gaagcagaaa agatgatcgt caactacttc      2280
gtcctctacc caaggtgcg cgattacatt cagagggtcg tatcggaagc gaaagaaaaa       2340
ggctatgtta gaacgctgtt tggaagaaaa agagacatac cacagctcat ggcccgggac      2400
aggaacacac aggctgaagg agaacgaatt gccataaaca ctcccataca gggtacagca      2460
gcggatataa taaagctggc tatgatagaa atagacaggg aactgaaaga aagaaaaatg      2520
agatcgaaga tgatcataca ggtccacgac gaactggttt ttgaagtgcc caatgaggaa      2580
aaggacgcgc tcgtcgagct ggtgaaagac agaatgacga atgtggtaaa gctttcagtg      2640
ccgctcgaag tggatgtaac catcggcaaa acatggtcgt ga                        2682
```

<210> SEQ ID NO 23
<211> LENGTH: 2682
<212> TYPE: DNA
<213> ORGANISM: Artificial Sequence
<220> FEATURE:
<223> OTHER INFORMATION: chimeric thermostable DNA polymerase CS6

<400> SEQUENCE: 23

```
atgaaagcta tgttaccatt attcgaaccc aaaggccggg tcctcctggt ggacggccac       60
cacctggcct accgcacctt cttcgccctg aagggcctca ccacgagccg ggcgaaccg      120
gtgcaggcgg tttacggctt cgccaagagc ctcctcaagg ccctgaagga ggacgggtac      180
aaggccgtct tcgtggtctt tgacgccaag gcccccttcct tccgcacga ggcctacgag      240
gcctacaagg caggccgcgc cccgacccc gaggacttcc ccggcagct cgccctcatc      300
aaggagctgt tggacctcct ggggtttact cgcctcgagg ttccgggctt tgaggcggac      360
gacgtcctcg ccacccctggc caagaaggcg aaagggagg ggtacgaggt gcgcatcctc      420
```

```
accgccgacc gggacccttta ccagctcgtc tccgaccgcg tcgccgtcct ccacccccgag    480 ggccacctca tcaccccgga gtggctttgg gagaagtacg gccttaagcc ggagcagtgg    540
gtggacttcc gcgccctcgt gggggacccc tccgacaacc tccccggggt caagggcatc    600
ggggagaaga ccgccctcaa gctcctcaag gagtggggaa gcctggaaaa tatcctcaag    660
aacctggacc gggtgaagcc ggaaagcgtc cgggaaagga tcaaggccca cctggaagac    720
cttaagctct ccttggagct ttcccgggtg cgctcggacc tcccccctgga ggtggacttc    780 gcccggaggc gggagcctga ccgggaaggg cttcgggcct ttttggagcg cttggagttc    840
ggcagcctcc tccacgagtt cggccttcta gaggagtccg aacccgttgg gtaccgtata    900
gttaaagacc tggttgaatt tgaaaaactc atagagaaac tgagagaatc tccttcgttc    960
gcgatcgctc ttgcgactag ttccctcgat cctttcgact gcgacattgt cggtatctct   1020
gtgtctttca aaccaaagga agcgtactac ataccactcc atcatagaaa cgcccagaac   1080
ctggacgaaa aagaggttct gaaaaagctc aaagaaattc tggaggaccc cggagcaaag   1140
atcgttggtc agaatttgaa attcgattac aaggtgttga tggtgaaggg tgttgaacct   1200
gttcctcctt acttcgacac gatgatacgc gcttaccttc ttgagccgaa cgaaaagaag   1260
ttcaatctgg acgatctcgc attgaaattt cttggataca aaatgacatc ttaccaagag   1320
ctcatgtcct tctcttttcc gctgtttggt ttcagttttg ccgatgttcc tgtagaaaaa   1380
gcagcgaact actcctgtga agatgcagac atcacctaca gactttacaa gaccctgagc   1440
ttaaaactcc acgaggcaga tctggaaaac gtgttctaca gatagaaat gccccttgtg   1500 aacgtgcttg cacggatgga actgaacggt gtgtatgtgg acacagagtt cctgaagaaa   1560
ctctcagaag agtacggaaa aaactcgaa gaactggcag aggaaatata caggatagct   1620
ggagagccgt tcaacataaa ctcaccgaag caggtttcaa ggatcctttt tgaaaaactc   1680
ggcataaaac cacgtggtaa aacgacgaaa acgggagact attcaacacg catagaagtc   1740
ctcgaggaac ttgccggtga acacgaaatc attcctctga ttcttgaata cagaaagata   1800
cagaaattga aatcaaccta catagacgct cttcccaaga tggtcaaccc aaagaccgga   1860
aggattcatg cttcttcaa tcaaacgggg actgccactg gaagacttag cagcagcgat   1920
cccaatcttc agaacctccc gacgaaaagt gaagagggaa aagaaatcag gaaagcgata   1980
gttcctcagg atccaaactg gtggatcgtc agtgccgact actcccaaat gaactgagg    2040 atcctcgccc atctcagtgg tgatgagaat cttttgaggg cattcgaaga gggcatcgac   2100
gtccacactc taacagcttc cagaatattc aacgtgaaac ccgaagaagt aaccgaagaa   2160
atgcgccgcg ctggtaaaat ggttaatttt tccatcatat acggtgtaac accttacggt   2220
ctgtctgtga ggcttggagt acctgtgaaa gaagcagaaa agatgatcgt caactacttc   2280
gtcctctacc caaaggtgcg cgattacatt cagagggtcg tatcggaagc gaagaaaaa    2340 ggctatgtta gaacgctgtt tggaagaaaa agagacatac cacagctcat ggccccgggac   2400 aggaacacac aggctgaagg agaacgaatt gccataaaca ctcccataca gggtacagca   2460
gcggatataa taaagctggc tatgatagaa atagacaggg aactgaaaga agaaaaaatg   2520
agatcgaaga tgatcataca ggtccacgac gaactggttt ttgaagtgcc caatgaggaa   2580
aaggacgcgc tcgtcgagct ggtgaaagac agaatgacga atgtggtaaa gctttcagtg   2640
ccgctcgaag tggatgtaac catcggcaaa acatggtcgt ga                     2682
```

<210> SEQ ID NO 24
<211> LENGTH: 26

```
<212> TYPE: PRT
<213> ORGANISM: Artificial Sequence
<220> FEATURE:
<223> OTHER INFORMATION: consensus sequence of region from polymerase
      domain of thermostable DNA polymerase, polymerase domain motif
      consensus sequence
<221> NAME/KEY: MOD_RES
<222> LOCATION: (1)...(26)
<223> OTHER INFORMATION: Xaa = any amino acid

<400> SEQUENCE: 24

Xaa Xaa Xaa Ala Gly Xaa Xaa Phe Asn Xaa Xaa Ser Xaa Xaa Gln Xaa
 1               5                  10                  15

Xaa Xaa Xaa Leu Phe Xaa Xaa Leu Xaa Xaa
            20                  25

<210> SEQ ID NO 25
<211> LENGTH: 16
<212> TYPE: PRT
<213> ORGANISM: Artificial Sequence
<220> FEATURE:
<223> OTHER INFORMATION: region from polymerase domain of mutant
      thermostable DNA polymerase, polymerase domain motif
<221> NAME/KEY: MOD_RES
<222> LOCATION: (1)...(1)
<223> OTHER INFORMATION: Xaa = Ile or Leu
<221> NAME/KEY: MOD_RES
<222> LOCATION: (2)...(2)
<223> OTHER INFORMATION: Xaa = Gln or Leu
<221> NAME/KEY: MOD_RES
<222> LOCATION: (3)...(3)
<223> OTHER INFORMATION: Xaa = Gln, His or Glu
<221> NAME/KEY: MOD_RES
<222> LOCATION: (4)...(4)
<223> OTHER INFORMATION: Xaa = Tyr, His or Phe
<221> NAME/KEY: MOD_RES
<222> LOCATION: (6)...(6)
<223> OTHER INFORMATION: Xaa = Glu, Gln or Lys
<221> NAME/KEY: MOD_RES
<222> LOCATION: (7)...(7)
<223> OTHER INFORMATION: Xaa = Ile, Leu or Tyr
<221> NAME/KEY: MOD_RES
<222> LOCATION: (8)...(8)
<223> OTHER INFORMATION: Xaa = Gln, Thr, Met, Gly or Leu
<221> NAME/KEY: MOD_RES
<222> LOCATION: (11)...(11)
<223> OTHER INFORMATION: Xaa = Lys or Gln
<221> NAME/KEY: MOD_RES
<222> LOCATION: (12)...(12)
<223> OTHER INFORMATION: Xaa = Ser or Asn
<221> NAME/KEY: MOD_RES
<222> LOCATION: (15)...(15)
<223> OTHER INFORMATION: Xaa = Ile or Val
<221> NAME/KEY: MOD_RES
<222> LOCATION: (16)...(16)
<223> OTHER INFORMATION: Xaa = Glu or Asp

<400> SEQUENCE: 25

Xaa Xaa Xaa Xaa Arg Xaa Xaa Xaa Lys Leu Xaa Xaa Thr Tyr Xaa Xaa
 1               5                  10                  15

<210> SEQ ID NO 26
<211> LENGTH: 13
<212> TYPE: PRT
<213> ORGANISM: Artificial Sequence
<220> FEATURE:
<223> OTHER INFORMATION: region from polymerase domain of mutant
      thermostable DNA polymerase, polymerase domain motif
<221> NAME/KEY: MOD_RES
<222> LOCATION: (7)...(7)
<223> OTHER INFORMATION: Xaa = Ser or Thr
<221> NAME/KEY: MOD_RES
<222> LOCATION: (8)...(8)
<223> OTHER INFORMATION: Xaa = Asp, Glu or Asn
```

```
<400> SEQUENCE: 26

Thr Gly Arg Leu Ser Ser Xaa Xaa Pro Asn Leu Gln Asn
1               5                   10

<210> SEQ ID NO 27
<211> LENGTH: 15
<212> TYPE: PRT
<213> ORGANISM: Artificial Sequence
<220> FEATURE:
<223> OTHER INFORMATION: region from polymerase domain of mutant
      thermostable DNA polymerase, polymerase domain motif
<221> NAME/KEY: MOD_RES
<222> LOCATION: (1)...(1)
<223> OTHER INFORMATION: Xaa = Gly, Asn or Asp
<221> NAME/KEY: MOD_RES
<222> LOCATION: (2)...(2)
<223> OTHER INFORMATION: Xaa = Trp or His
<221> NAME/KEY: MOD_RES
<222> LOCATION: (3)...(3)
<223> OTHER INFORMATION: Xaa = Trp, Ala, Leu or Val
<221> NAME/KEY: MOD_RES
<222> LOCATION: (4)...(4)
<223> OTHER INFORMATION: Xaa = Ile or Leu
<221> NAME/KEY: MOD_RES
<222> LOCATION: (5)...(5)
<223> OTHER INFORMATION: Xaa = Val, Phe or Leu
<221> NAME/KEY: MOD_RES
<222> LOCATION: (6)...(6)
<223> OTHER INFORMATION: Xaa = Ser, Ala, Val or Gly
<221> NAME/KEY: MOD_RES
<222> LOCATION: (7)...(7)
<223> OTHER INFORMATION: Xaa = Ala or Leu

<400> SEQUENCE: 27

Xaa Xaa Xaa Xaa Xaa Xaa Xaa Asp Tyr Ser Gln Ile Glu Leu Arg
1               5                   10                  15

<210> SEQ ID NO 28
<211> LENGTH: 30
<212> TYPE: DNA
<213> ORGANISM: Artificial Sequence
<220> FEATURE:
<223> OTHER INFORMATION: oligonuceotide template primer for M13mp18 (M13
      DNA) extension assay screen

<400> SEQUENCE: 28
gggaagggcg atcggtgcgg gcctcttcgc                                     30

<210> SEQ ID NO 29
<211> LENGTH: 21
<212> TYPE: PRT
<213> ORGANISM: Artificial Sequence
<220> FEATURE:
<223> OTHER INFORMATION: region from polymerase domain of unmodified
      form of thermostable DNA polymerase, polymerase domain motif
<221> NAME/KEY: MOD_RES
<222> LOCATION: (3)...(3)
<223> OTHER INFORMATION: Xaa = His, Glu or Gln
<221> NAME/KEY: MOD_RES
<222> LOCATION: (4)...(4)
<223> OTHER INFORMATION: Xaa = any amino acid
<221> NAME/KEY: MOD_RES
<222> LOCATION: (6)...(6)
<223> OTHER INFORMATION: Xaa = Asn or His
<221> NAME/KEY: MOD_RES
<222> LOCATION: (7)...(7)
<223> OTHER INFORMATION: Xaa = Leu or Ile
<221> NAME/KEY: MOD_RES
<222> LOCATION: (8)...(8)
<223> OTHER INFORMATION: Xaa = any amino acid
<221> NAME/KEY: MOD_RES
<222> LOCATION: (10)...(10)
<223> OTHER INFORMATION: Xaa = any amino acid
<221> NAME/KEY: MOD_RES
```

-continued

```
<222> LOCATION: (11)...(11)
<223> OTHER INFORMATION: Xaa = Asp, Lys or Thr
<221> NAME/KEY: MOD_RES
<222> LOCATION: (13)...(13)
<223> OTHER INFORMATION: Xaa = Leu or Val
<221> NAME/KEY: MOD_RES
<222> LOCATION: (14)...(15)
<223> OTHER INFORMATION: Xaa = any amino acid
<221> NAME/KEY: MOD_RES
<222> LOCATION: (16)...(16)
<223> OTHER INFORMATION: Xaa = Val, Ile or Leu
<221> NAME/KEY: MOD_RES
<222> LOCATION: (18)...(18)
<223> OTHER INFORMATION: Xaa = Phe or Tyr
<221> NAME/KEY: MOD_RES
<222> LOCATION: (19)...(19)
<223> OTHER INFORMATION: Xaa = Asp or Glu
<221> NAME/KEY: MOD_RES
<222> LOCATION: (20)...(20)
<223> OTHER INFORMATION: Xaa = Lys or Glu
<221> NAME/KEY: MOD_RES
<222> LOCATION: (21)...(21)
<223> OTHER INFORMATION: Xaa = Leu or Gln

<400> SEQUENCE: 29

Ala Gly Xaa Xaa Phe Xaa Xaa Xaa Ser Xaa Xaa Gln Xaa Xaa Xaa Xaa
1               5                   10                  15

Leu Xaa Xaa Xaa Xaa
            20

<210> SEQ ID NO 30
<211> LENGTH: 8
<212> TYPE: PRT
<213> ORGANISM: Artificial Sequence
<220> FEATURE:
<223> OTHER INFORMATION: conserved DNA polymerase active site Motif A

<400> SEQUENCE: 30

Asp Tyr Ser Gln Ile Glu Leu Arg
1               5

<210> SEQ ID NO 31
<211> LENGTH: 26
<212> TYPE: PRT
<213> ORGANISM: Artificial Sequence
<220> FEATURE:
<223> OTHER INFORMATION: region from polymerase domain of chimeric
      thermostable DNA polymerase CS5

<400> SEQUENCE: 31

Tyr Arg Ile Ala Gly Glu Pro Phe Asn Ile Asn Ser Pro Lys Gln Val
1               5                   10                  15

Ser Arg Ile Leu Phe Glu Lys Leu Gly Ile
            20                  25

<210> SEQ ID NO 32
<211> LENGTH: 26
<212> TYPE: PRT
<213> ORGANISM: Artificial Sequence
<220> FEATURE:
<223> OTHER INFORMATION: region from polymerase domain of chimeric
      thermostable DNA polymerase CS6

<400> SEQUENCE: 32

Tyr Arg Ile Ala Gly Glu Pro Phe Asn Ile Asn Ser Pro Lys Gln Val
1               5                   10                  15

Ser Arg Ile Leu Phe Glu Lys Leu Gly Ile
            20                  25
```

```
<210> SEQ ID NO 33
<211> LENGTH: 21
<212> TYPE: PRT
<213> ORGANISM: Artificial Sequence
<220> FEATURE:
<223> OTHER INFORMATION: region from polymerase domain of modified
      improved thermostable DNA polymerase, polymerase domain motif
<221> NAME/KEY: MOD_RES
<222> LOCATION: (3)...(3)
<223> OTHER INFORMATION: Xaa = His, Glu or Gln
<221> NAME/KEY: MOD_RES
<222> LOCATION: (4)...(4)
<223> OTHER INFORMATION: Xaa = any amino acid
<221> NAME/KEY: MOD_RES
<222> LOCATION: (6)...(6)
<223> OTHER INFORMATION: Xaa = Asn or His
<221> NAME/KEY: MOD_RES
<222> LOCATION: (7)...(7)
<223> OTHER INFORMATION: Xaa = Leu or Ile
<221> NAME/KEY: MOD_RES
<222> LOCATION: (8)...(8)
<223> OTHER INFORMATION: Xaa = any amino acid
<221> NAME/KEY: MOD_RES
<222> LOCATION: (10)...(10)
<223> OTHER INFORMATION: Xaa = any amino acid
<221> NAME/KEY: MOD_RES
<222> LOCATION: (11)...(11)
<223> OTHER INFORMATION: Xaa = Asp, Lys or Thr
<221> NAME/KEY: MOD_RES
<222> LOCATION: (13)...(13)
<223> OTHER INFORMATION: Xaa = Leu or Val
<221> NAME/KEY: MOD_RES
<222> LOCATION: (14)...(15)
<223> OTHER INFORMATION: Xaa = any amino acid
<221> NAME/KEY: MOD_RES
<222> LOCATION: (16)...(16)
<223> OTHER INFORMATION: Xaa = Val, Ile or Leu
<221> NAME/KEY: MOD_RES
<222> LOCATION: (18)...(18)
<223> OTHER INFORMATION: Xaa = Phe or Tyr
<221> NAME/KEY: MOD_RES
<222> LOCATION: (20)...(20)
<223> OTHER INFORMATION: Xaa = Lys or Glu
<221> NAME/KEY: MOD_RES
<222> LOCATION: (21)...(21)
<223> OTHER INFORMATION: Xaa = Leu or Gln

<400> SEQUENCE: 33

Ala Gly Xaa Xaa Phe Xaa Xaa Xaa Ser Xaa Xaa Gln Xaa Xaa Xaa Xaa
1               5                   10                  15

Leu Xaa Gly Xaa Xaa
            20
```